United States Patent
Cohen et al.

(10) Patent No.: US 11,597,908 B2
(45) Date of Patent: Mar. 7, 2023

(54) FREEZE-RESISTANT YEAST AND USES THEREOF

(71) Applicant: NextFerm Technologies Ltd., Yokneam Illit (IL)

(72) Inventors: Tzafra Cohen, Haifa (IL); Moran Gendelman, Misgav (IL); Marina Khutorian, Nesher (IL); Sivan Mor, Tirat Carmel (IL); Paz Shemesh, Tiberias (IL); Yael Lifshitz-Medved, Zikhron Yaakov (IL)

(73) Assignee: NextFerm Technologies Ltd., Yokneam Illit (IL)

( * ) Notice: Subject to any disclaimer, the term of this patent is extended or adjusted under 35 U.S.C. 154(b) by 265 days.

(21) Appl. No.: 16/093,243

(22) PCT Filed: Apr. 12, 2017

(86) PCT No.: PCT/IB2017/000419
§ 371 (c)(1),
(2) Date: Oct. 12, 2018

(87) PCT Pub. No.: WO2017/178879
PCT Pub. Date: Oct. 19, 2017

(65) Prior Publication Data
US 2019/0119763 A1     Apr. 25, 2019

(30) Foreign Application Priority Data

Apr. 12, 2016  (EP) .................................. 16164933
Nov. 4, 2016  (EP) .................................. 16197393

(51) Int. Cl.
*C12N 1/18*     (2006.01)
*A21D 8/04*     (2006.01)
(Continued)

(52) U.S. Cl.
CPC ............. *C12N 1/185* (2021.05); *A21D 6/001* (2013.01); *A21D 8/047* (2013.01); *C12N 1/14* (2013.01); *C12N 1/18* (2013.01); *C12R 2001/865* (2021.05)

(58) Field of Classification Search
CPC ................................ C12R 1/865; A21D 8/047
See application file for complete search history.

(56) References Cited

U.S. PATENT DOCUMENTS 5,352,606 A * 10/1994 Takano .................. A21D 8/047
                                                        426/18
5,801,049 A *  9/1998 Endo ........................ C12N 1/865
                                                        426/19
(Continued)

FOREIGN PATENT DOCUMENTS

CA      1 299 435 C    4/1992
CN      1982436 A      6/2007
(Continued)

OTHER PUBLICATIONS

Canadian Office Action issued in Canadian Application No. 3,020,653 dated Feb. 13, 2020 (four (4) pages).
(Continued)

*Primary Examiner* — Stephanie A Cox
(74) *Attorney, Agent, or Firm* — Crowell & Moring LLP

(57) ABSTRACT

Freeze-resistant baker's yeast (*Saccharomyces cerevisiae*) strains and uses thereof. For example, for the preparation of fresh or frozen dough products, e.g., bread. The freeze-resistant baker's yeast strains, which are, e.g., obtainable from specific deposited strains, e.g., by breeding these strains with each other or with other *Saccharomyces cerevisiae* strains. Methods of using said strains or methods of
(Continued)

preparing a dough or a dough product or a yeast product are also provided.

11 Claims, 4 Drawing Sheets

Specification includes a Sequence Listing.

(51) Int. Cl.
*A21D 6/00* (2006.01)
*C12N 1/14* (2006.01)
*C12R 1/865* (2006.01)

(56) References Cited

U.S. PATENT DOCUMENTS

| | | |
|---|---|---|
| 2006/0134268 A1 | 6/2006 | Nagasawa |
| 2019/0119763 A1 | 4/2019 | Cohen et al. |

FOREIGN PATENT DOCUMENTS

| | | |
|---|---|---|
| CN | 101171936 A | 5/2008 |
| CN | 101575577 A | 11/2009 |
| CN | 103194401 A | 7/2013 |
| CN | 103275881 A | 9/2013 |
| CN | 103497903 A | 1/2014 |
| CN | 104017742 A | 9/2014 |
| EP | 1 209 225 A1 | 5/2002 |
| EP | 1 541 671 A1 | 6/2005 |
| EP | 3 318 646 B1 | 2/2019 |
| JP | 6-70673 A | 3/1994 |
| RU | 2 756 307 C2 | 9/2021 |
| WO | WO 2017/178879 A1 | 10/2017 |

OTHER PUBLICATIONS

Jianzhi Zhang, "Rates of Conservative and Radical Nonsynonymous Nucleotide Substitutions in Mammalian Nuclear Genes", Journal of Molecular Evolution, 2000, vol. 50, No. 1, pp. 56-68, (13 pages).
T. Boekhout and V. Robert, "Yeasts in Food: Beneficial and Detrimental Aspects", Woodhead Publishing in Food Science and Technology, 2003, pp. 297, (two (2) pages).
Byong H. Lee, "Fundamentals of Food Biotechnology", 2014, Wiley-Blackwell, pp. 184 (four (4) pages).
Sahin et al., "Physical Properties of Foods", Springer, p. 20 (two (2) pages).
Giudici et al., "Strategies and Perspectives for Genetic Improvement of Wine Yeasts", Appl Microbiol Biotechnol, 2005, vol. 66, pp. 622-628, (seven (7) pages).
Steensels et al., "Improving Industrial Yeast Strains: Exploiting Natural and Artificial Diversity", 2014, FEMS Microbiol Rev, vol. 38, pp. 947-995, (49 pages).
Matsutani et al., "Physical and Biochemical Properties of Freeze-Tolerant Mutants of a Yeast *Saccharomyces Cerevisiae*", 1990, Journal of Fermentation and Bioengineering, vol. 70, No. 4, pp. 275-276, (two (2) pages).
Nakagawa et al., "Construction From a Single Parent of Baker's Yeast Strains with High Freeze Tolerance and Fermentative Activity in Both Lean and Sweet Doughs", Oct. 1994, Applied and Environmental Microbiology, vol. 60, No. 10, pp. 3499-3502 (four (4) pages).
Tanghe et al., "Aquaporin Expression Correlates with Freeze Tolerance in Baker's Yeast, and Overexpression Improves Freeze Tolerance in Industrial Strains", Dec. 2002. Applied and Environmental Microbiology, vol. 68, No. 12, pp. 5981-5989 (nine (9) pages).
Chandra J. Panchal, "Yeast Strain Selection", 1990, Marcel Dekker Inc., p. 140 (two (2) pages).
Müller-Auffermann et al., "Evaluation and Development of An Alternative Analysis Method for Rapid Determination of Yeast Vitality", Jun. 2014, Brewing Science, vol. 67, pp. 72-80 (nine (9) pages).
Kulp et al., "Handbook of Dough Fermentations", 2003, Marcel Dekker Inc. (303 pages).
International Search Report (PCT/ISA/210) issued in PCT Application No. PCT/IB2017/000419 dated Aug. 17, 2017 (nine (9) pages).
Teunissen A. et al., "Isolation and Characterization of a Freeze-Tolerant Diploid Derivative of an Industrial Baker's Yeast Strain and Its Use in Frozen Doughs", Applied and Environmental Microbiology, Oct. 1, 2002, pp. 4780-4787, vol. 68, No. 10, XP055309217 (eight (8)pages).
Tanghe A. et al., "Identification of Genes Responsible for Improved Cryoresistance in Fermenting Yeast Cells", International Journal of Food Microbiology, Apr. 10, 2000, pp. 259-262, vol. 55, No. 1-3, XP027347039 (four (4) pages).
Hino A. et al., "New Freeze Tolerant Yeast for Frozen Dough Preparations", Cereal Chemistry, AACC International Inc., Jan. 1, 1987, pp. 269-275, vol. 64, No. 4, XP002098766 (seven (7) pages).
Oda Y. et al., "Selection of Yeasts for Breadmaking by the Frozen-Dough Method", Applied and Environmental Microbiology, Tokyo Research Laboratory, Oct. 1, 1986, pp. 941-943, vol. 52, No. 4, Machida-shi, Tokyo, JP, XP055309321 (three (3) pages).
English-language Written Opinion (PCT/ISA/237) issued in PCT Application No. PCT/IB2017/000419 dated Oct. 19, 2017 (ten (10) pages).
Russian-language Office Action issued in Russian Application No. 2018139496 dated Sep. 23, 2020 with English translation (16 pages).
Bannitsyna et al. "Primeneniye drozhzhey i produktov ikh pererabotki v pishchevoy promyshlennosti. Vestnik Voronezhskogo gosudarstvennogo agrarnogo universiteta", 2015, pp. 176-183, vol. N4, No. 47, (eight (8) pages).
European Office Action issued in European Application No. 17725340.8 dated Nov. 4, 2020 (six (6) pages).
Hebrew-language Office Action issued in Israeli Application No. 262248 dated Jun. 14, 2020 with English translation (eight (8) pages).
Canadian Office Action issued in Canadian Application No. 3020653 dated Feb. 22, 2021 (six (6) pages).
Korean-language Office Action issued in Korean Application No. 10-2018-7032668 dated Feb. 23, 2021 with English translation (11 pages).
Russian-language Office Action issued in Russian Application No. 2018139496 dated Feb. 17, 2021 with English translation (13 pages).
Hebrew-language Office Action issued in Israeli Application No. 262248 dated Jul. 27, 2021 (seven (7) pages).
Chinese-language Office Action issued in Chinese Application No. 201780036306.4 dated Dec. 13, 2021 (10 pages).
Spanish-language Office Action issued in Mexican Application No. MX/a/2018/012582 dated Dec. 8, 2021 (five (5) pages).
European Communication pursuant to Article 94(3) EPC issued in European Application No. 17 725 340.8 dated Feb. 16, 2022 (four (4) pages).
Canadian Office Action issued in Canadian Application No. 3,020,653 dated Mar. 4, 2022 (five (5) pages).
Chinese-language Office Action issued in Chinese Application No. 2017800363064 dated May 30, 2022 with English translation (11 pages).

\* cited by examiner

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctgtatggtt cgccgtttat                                         20

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ggtaatctgt gggatgtaac tg                                      22

<210> SEQ ID NO 3
<211> LENGTH: 18
<212> TYPE: DNA

```
<213> ORGANISM: Artificial Sequence
<220> FEATURE:
<223> OTHER INFORMATION: Primer

<400> SEQUENCE: 3
attgcctctc agtatcgt                                                         18

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
cacaaatctt ccaaaccac                                                        19

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cgctgtagca aagcaaaaag                                                       20

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gcaatgaccg taggagtga                                                        19

<210> SEQ ID NO 7
<211> LENGTH: 604
<212> TYPE: DNA
<213> ORGANISM: Saccharomyces cerevisiae

<400> SEQUENCE: 7
ctgtatggtt cgccgtttat tttctaagca ccgttttttta ttcatatttt tataatgcaa           60
ctcctataga atatagatgt ttcgtgtttt taattcctgc tatgactttg tgtcaatggt          120
atgtgaacta acaactgtgt ggtagtttgg gatggtacgt aaaggtgttc gtgattatat          180
aagcaatctt aaaatatttg tatcgcacca tgaggtgccc aataatgaaa tgaaaattac          240
tattatgaac tatactaaaa agatgaaact tttttatcaa tcccaggttc ttttacttat          300
tatttttgga tataagaaca aaatcggatt tcccatgctt tttctcaatg tctatatgaa          360
atcttttcga acagccagt acatgtaaca attatgatac gaacttgatc ggtaacccat           420
aaataacagg agctgcgccg ttcaagtaac gtagatggca tacacctcta gatttagaga          480
cggcatatga aacagatagg ctattaccat tcaaatcgtc agtattacag cgaaatccca          540
tcttttcaaa aagttcctcg ctaaatttat caatatcttt gtcagttaca tcccacagat          600
tacc                                                                      604

<210> SEQ ID NO 8
<211> LENGTH: 372
<212> TYPE: DNA
<213> ORGANISM: Saccharomyces cerevisiae
```

-continued

```
<400> SEQUENCE: 8
attgcctctc agtatcgtaa ttctatgtgg gtatctgact tcatggcaa ctaggtaaga        60 tacagtttca acagaataat atcctctatc cacgtaatca cccatgaaaa ggtaattggt       120
gtcaggacaa ggaccaccaa tcttgaaaag ttctaacaag tcatggaatt gaccgtgtac       180
gtcaccacaa atagtaacag gcacattaat tggtttaaca ttttcctcga actgcaacac       240
gtccaccgcc attttacata gtcgtgctac atcgtcttct gatagtggct cgcatttact       300
caaatgctca atccattggt caagctgatt tatatttgtg ttattcagtt ctagtggttt       360
ggaagatttg tg                                                           372

<210> SEQ ID NO 9
<211> LENGTH: 616
<212> TYPE: DNA
<213> ORGANISM: Saccharomyces cerevisiae

<400> SEQUENCE: 9
cgctgtagca aagcaaaaag tttctgattc aaaataagtc acctactctt agcgcatttt        60
tattgtatat aaaggcattt aatgtaattt atagagcatt ataaatcgta acaactactg       120
cagtatgagt ttcatgaatt catttctcga tatcttatga atatacacag gtatatatgt       180
atattcatgt taaacgcctt tcgaattgtt cgttggcttt ttttgtgaaa ttatctcggg       240
aaaagggcga aattatatcg ttttgccgtt gatattttga aaaggaataa aagatcatga       300
aaaaaataag aaaggcaatt cgacgcattt ctctcagcaa gctattcttt acttttgaag       360
aataaaatat ttgagtaaaa aggttaagac aatatagtcg gaagcagttc tgcgggatct       420
gaaggaattg cggaataatg agatttcacg atagtatact tatcttcttt tctttggcat       480
cgctttatca acatgttcat ggtgcaagac aagtcgttcg tccaaaggag aaaatgacta       540
cttcagaaga agttaaacct tggttacgta cggtttatgg aagtcaaaaa gaattagtca       600
ctcctacggt cattgc                                                       616
```

FREEZE-RESISTANT YEAST AND USES THEREOF

CROSS REFERENCE TO RELATED APPLICATIONS

This application is a U.S. National Stage Application of International Application No. PCT/IB2017/000419, filed on Apr. 12, 2017, which claims priority to EP 16164933.0, filed on Apr. 12, 2016, and EP 16197393.8, filed on Nov. 4, 2016, all of which are expressly incorporated herein by reference in their entireties.

BACKGROUND ART

The present invention relates to novel freeze-resistant baker's yeast (*Saccharomyces cerevisiae*) strains and uses thereof, for example for the preparation of fresh or frozen dough products, e.g., bread. It provides freeze-resistant baker's yeast strains, which are, e.g., obtainable from specific deposited strains, e.g., by breeding these strains with each other or with other *Saccharomyces cerevisiae* strains. The invention also relates to methods of using said strains or methods of preparing a dough or dough product or yeast product, as well as such products.

Both as convenience products for home use and as commercial half-finished products, frozen doughs or dough products, e.g., for bread, rolls or pastry, are becoming more and more important. Accordingly, freeze-resistance of baker's yeast is an increasingly important parameter. Classical yeast strains may be used for preparation of frozen dough, but typically, a two to threefold excess of yeast is used for preparation of such doughs, which may negatively affect the flavor of the baked product.

Furthermore, shelf-life of frozen yeast products is much longer than shelf-life of non-frozen, fresh or dried yeasts. For such applications, freeze-resistance of yeast also plays an important role.

Special freeze-resistant yeast strains are already available (e.g., U.S. Pat. No. 5,352,606 B1, EP 1 209 225 A1, EP 1 541 671 A1), however, there is a need in the art for baker's yeast strains which are yet better adapted to freezing, e.g., which have a higher survival rate and/or better performance, such as increased fermentative ability after freezing.

This problem is solved by the present invention, in particular, by the subject matter of the claims.

SUMMARY OF INVENTION AND DETAILED DESCRIPTION

Figure 1A:
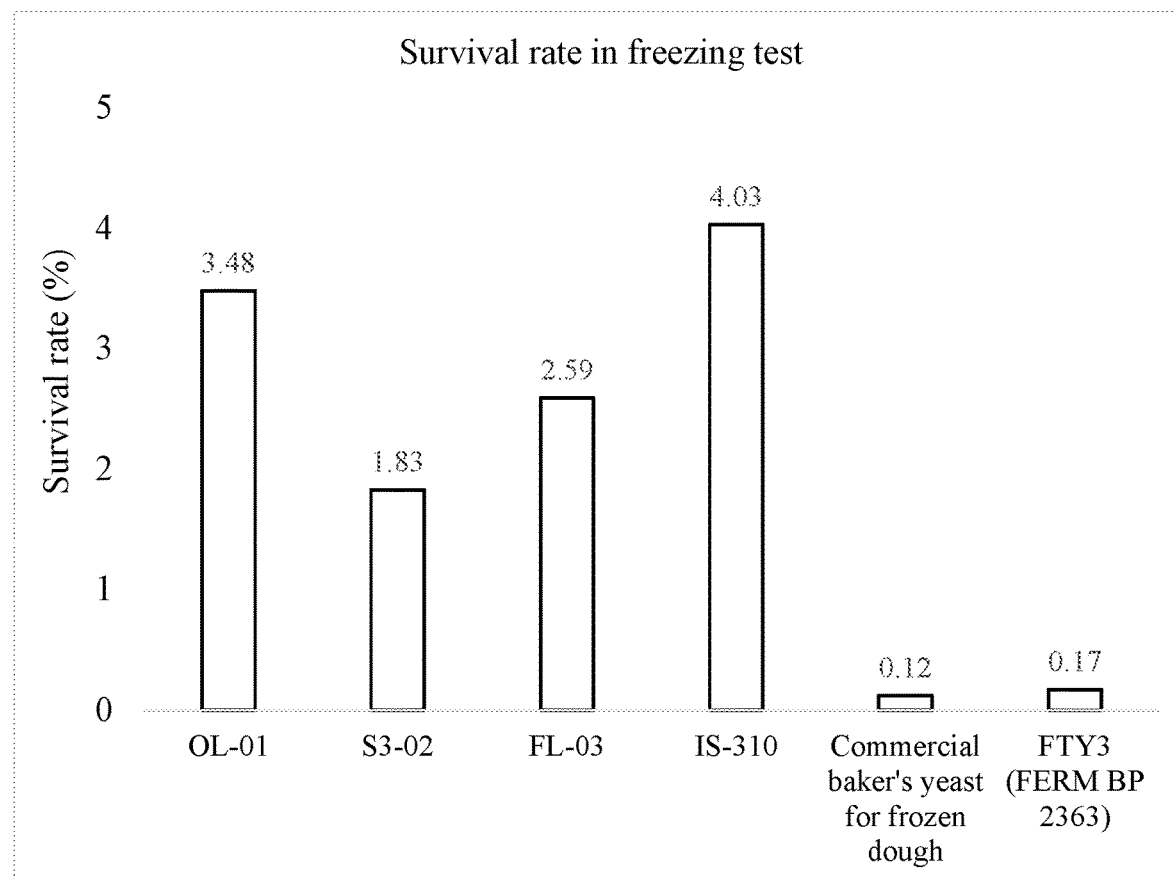
FIG. 1 Survival rate of yeast strains of the invention compared with state of the art commercial yeast strains.

The present invention provides a yeast strain obtainable from strains OL-01 deposited as NCYC 4095, S3-02 deposited as NCYC 4094, FL-03 deposited as NCYC 4105, IS-310 deposited as NCYC 4106, CC-05 deposited as NCYC 4128 and KF-06 deposited as NCYC-4129. The yeast strain of the invention may be a baker's yeast strain.

For example, the strain of the invention may be obtainable by breeding between first strain selected from the group consisting of OL-01, S3-02, FL-03, IS-310, CC-05 and KF-06 and a second *Saccharomyces cerevisiae* strain, which may also be a baker's yeast strain. Brewer's yeast may also be used for breeding, e.g., if a freeze-resistant strain suitable for brewing is desired. Preferably, however, both strains used in breeding are baker's yeast strains. The second *Saccharomyces cerevisiae* strain may also be selected from the group comprising OL-01, S3-02, FL-03, IS-310, CC-05 and KF-06. For example, OL-01 may be used for breeding with OL-01, S3-02, FL-03, IS-310, CC-05, KF-06 or another baker's yeast strain. S3-02 may be used for breeding with OL-01, S3-02, FL-03, IS-310, CC-05, KF-06 or another baker's yeast strain. FL-03 may be used for breeding with OL-01, S3-02, FL-03, IS-310, CC-05, KF-06 or another baker's yeast strain. IS-310 may be used for breeding with OL-01, S3-02, FL-03, IS-310, CC-05, KF-06 or another baker's yeast strain. CC-05 may be used for breeding with OL-01, S3-02, FL-03, IS-310, CC-05, KF-06 or another baker's yeast strain. KF-06 may be used for breeding with OL-01, S3-02, FL-03, IS-310, CC-05, KF-06 or another baker's yeast strain. Breeding may be, e.g., by spore to spore or spore to cell or cell to cell hybridization. The other baker's yeast strain may be a freeze-resistant strain, e.g., disclosed by U.S. Pat. No. 5,352,606 B1, EP 1 209 225 A1, EP 1 541 671 A1, such as FTY-3 (BP FERM 2363). It may also be a non-freeze-resistant strain having other specific characteristics, e.g., osmotolerance, which may be useful for adding said specific desirable characteristics to a yeast of the invention. Preferably, after inter-breeding (e.g., hybridization), one or more rounds of selection for freeze-resistance are performed.

Of course, the strain may be one of the deposited strains, OL-01, S3-02, FL-03, IS-310, CC-05 or KF-06. Preferably, the strain is OL-01, and more preferably, the strain is CC-05.

The invention also provides a baker's yeast strain of the invention, e.g., OL-01, S3-02, FL-03, IS-310, CC-05 or KF-06, wherein preferably, the strain is CC-05, wherein the strain comprises mutations in at least two genes selected from the group consisting of:

a) Gene YDL248W named COS7 located at Chromosome IV, wherein the mutation preferably is a deletion;

b) Gene YJR155W named AAD10 located at Chromosome X, wherein the mutation preferably is a deletion;

c) Gene YDL245C named HXT15 located at Chromosome IV, wherein the mutation preferably is a deletion;

d) Gene YJR151C named DAN4 located at Chromosome X, wherein the mutation preferably a deletion and/or a genomic rearrangement and/or an introduction of a stop codon;

e) Gene YDR420W named HKR1 located at Chromosome IV, wherein the mutation preferably is at least one point mutation leading to an exchange of amino acids.

wherein the mutations are present in all alleles of said genes.

Preferably, the yeast strain comprises mutations in three or more, or four or more or five of said genes. Most preferably, the yeast strain comprises all cited mutations.

Preferably, the strain of the invention comprises mutations in at least two genes selected from the group consisting of:

a) Gene YDL248W named COS7 located at Chromosome IV, wherein the mutation is a deletion downstream to position 2232 (wherein the deletion, e.g., has a length of at least 150 basepairs);

b) Gene YJR155W named AAD10 located at Chromosome X, wherein the mutation is at least one deletion downstream to position 727404 (wherein the total length of deletion(s), is, e.g., at least 360 basepairs);

c) Gene YDL245C named HXT15 located at Chromosome IV, wherein the mutation is at least one deletion downstream to position 11657 (wherein the total length of deletion(s), is, e.g., at least 400 basepairs);

d) Gene YJR151C named DAN4 located at Chromosome X, wherein the mutation is introduction of one or two stop codons, preferably, at amino acid position 342 (exchange of Serine to stop codon) and/or at amino acid position 53 (exchange of Tyrosine to stop codon) and/or at least partial deletion and/or genomic rearrangement, e.g., between coordinates of Chromosome X:714,902-715,267;

e) Gene YDR420W named HKR1 located at Chromosome IV, wherein the mutation is at least one point mutation leading to an amino acids exchange, wherein the mutation preferably is selected from at least one, preferably all of a group consisting of a mutation at position 1308583 and at position 1308589, resulting in exchange from Serine to Proline and/or a mutation at position 1308951 and at position 1309390 resulting in exchange from Phenylalanine to Leucine, wherein the mutations are present in all alleles of said genes.

Preferably, the yeast strain comprises mutations in two or more, three or more, or four or more or five of said genes. Most preferably, the yeast strain comprises all cited mutations.

In the context of the invention, point mutations leading to an amino acids exchange preferably significantly change the biochemical properties of the amino acid, preferably, they are non-conservative mutations (as defined by Zhang, J Mol Evol 2000, 50(1): 56-68). Such point mutations may lead to functional inactivation of the gene product.

It is believed that the deletions and/or stop codon found in the analysed strains lead to functional inactivation of the respective gene products, and mutations leading to such functional inactivation are preferred in the invention. Of course, it is possible to inactivate the gene product by different mutations. Therefore, in one embodiment, a yeast strain of the invention comprises mutations leading to functional inactivation of the gene products of at least two (preferably, three or more, four or more or all) of the following genes in all alleles:

a) Gene YDL248W named COS7 located at Chromosome IV, wherein the mutation preferably is a deletion;

b) Gene YJR155W named AAD10 located at Chromosome X, wherein the mutation preferably is a deletion;

c) Gene YDL245C named HXT15 located at Chromosome IV, wherein the mutation preferably is a deletion;

d) Gene YJR151C named DAN4 located at Chromosome X, wherein the mutation preferably is introduction of a stop codon and/or a deletion and/or a genomic rearrangement;

e) Gene YDR420W named HKR1 located at Chromosome IV, wherein the mutation preferably is at least one point mutation leading to an exchange of an amino acid.

Accordingly, preferred yeast strains of the invention may be identified and differentiated from conventional yeast strains by analyzing for presence of the mutations specified herein, e.g., by PCR.

Preferred baker's yeast strains of the invention (e.g., CC-05 or KF-06) comprise at least two sequences selected from the group consisting of i) SEQ ID NO: 7 or a sequence variant comprising a change of at most three, preferably, at most two or at most one, base pairs thereto, wherein said sequence or one of said sequence variants is present in each allele, ii) SEQ ID NO: 8 or a sequence variant comprising a change of at most three, preferably, at most two or at most one, base pairs thereto, wherein said sequence or one of said sequence variants is present in each allele and iii) SEQ ID NO: 9 or a sequence variant comprising a change of at most three, preferably, at most two or at most one, base pairs thereto, wherein said sequence or one of said sequence variants is present in each allele, wherein, preferably, the strain comprises all three of said sequences. In one embodiment, said strain is homozygous with regard to SEQ ID NO: 8 and SEQ ID NO: 9 and heterozygous with regard to SEQ ID NO: 7.

In a preferred embodiment, the strain comprises three sequences from the group consisting of i) SEQ ID NO: 7 or a sequence variant comprising a change of at most one base pair thereto, wherein said sequence or one of said sequence variants is present in each allele, ii) SEQ ID NO: 8 or a sequence variant comprising a change of at most one base pair thereto, wherein said sequence or one of said sequence variants is present in each allele and iii) SEQ ID NO: 9 or a sequence variant comprising a change of at most one base pair thereto, wherein said sequence or one of said sequence variants is present in each allele.

In one embodiment, said strain comprises two sequences selected from the group consisting of SEQ ID NO: 8 and SEQ ID NO: 9 in all alleles, and SEQ ID NO: 7 is present in at least one allele, with a variant having one base pair changed in at least one other allele.

Said yeast strain of the invention preferably is freeze-resistant and suitable for baking, e.g. for baking bread.

The invention also provides a baker's yeast strain of the invention, wherein the strain is capable of surviving a regimen comprising freezing and thawing with a survival rate of at least 1%, wherein the regimen may be as follows:

a) the yeast strain is grown on YPD medium for 15 h in a shaker-incubator at 30° C. and 200 rpm, b) the yeast culture is harvested and re-suspended in YPD medium to a concentration of 5 $OD_{600}$, c) 5 mL yeast suspensions in 50 mL tubes (typically, centrifuge tubes) are incubated at −20° C. for 48-72h, d) followed by four freezing/thawing cycles, each freezing/thawing cycle comprising 1.5 h at 30° C. and 200 rpm, and at least 1 h at −20° C., wherein the survival rate is determined as the number of viable yeast colonies after said freeze/thawing cycles/the number of viable yeast colonies before said freeze/thawing cycles ×100%, and wherein the number of viable yeast colonies is measured using seeding decimal dilutions of yeast suspensions on YPD agar plates and incubation at 30° C. for 48 hours.

Yeast strains having a survival rate of at least 0.5% in said regimen are advantageous freeze-resistant strains of the invention. Preferably, the survival rate in said regimen is at least 1%, at least 1.25%, at least 1.5%, at least 1.75%, at least 2%, at least 2.5%, at least 3%, at least 3.5% or at least 4%., e.g., 0.5%-4.5%. The inventors showed that yeast strains of the invention have a survival rate of at least 1.2% or at least 1.5% in said regimen, whereas commercially available yeast for frozen dough and the freeze-resistant strain FTY3 (FERM BP 2363, cf. U.S. Pat. No. 5,352,606 B1) only have a survival rate of 0.12% or 0.26% and 0.17%, respectively (FIG. 1).

Preferably, the yeast strain obtainable from any of strains OL-01, S3-02, FL-03, IS-310, CC-05 and KF-06 e.g., by breeding between them as described above, has a survival rate in the described regimen of at least 0.5%, at least 1%, at least 1.25%, at least 1.5%, at least 1.75%, at least 2%, at least 2.5%, at least 3%, at least 3.5% or at least 4%., e.g., 0.5%-4.5%.

The yeast strain obtainable from any of strains OL-01, S3-02, FL-03, IS-310, CC-05 and KF-06, e.g., by breeding between them as described above, preferably demonstrates a survival rate of at least 54% preferably at least 64%, preferably at least 74%, and more preferably at least 84% of the average survival rate of the original parents.

The invention also provides a method of preparing a freeze-resistant yeast strain, in particular, baker's yeast strain of the invention, comprising steps of a) breeding between a yeast strain of the invention, such as OL-01, S3-02, FL-03, IS-310, CC-05 and KF-06 and a second yeast strain selected from the group comprising OL-01, S3-02, FL-03, IS-310, CC-05 and KF-06; and b) selecting the resulting yeast strains for freeze-resistance, and, optionally, c) selecting the resulting freeze-resistant yeast strains for their fermentative activity.

The fermentative performance of a yeast strain of the invention can advantageously be assessed in a liquid flour suspension (LFS), e.g., in the method as briefly described below, or in more detail in Example 5. This test advantageously assesses both freeze-resistance and fermentative performance.

Fermentative performance can, e.g., be tested by a method comprising propagating yeast cultures on 5 mL YPD substrate for 15 h in a shaker-incubator at 30° C. and at 200 rpm, followed by freezing the cultures at −18° C. for 3 days. One culture from each strain tested immediately for fermentative performance in a LFS e.g., non-sugar liquid flour suspension as described in Example 5. In brief, cultures were washed twice with distilled water and incubated with LFS for 1.5 hours. The LFS sample, after a certain time, forms two phases, a flour sediment at the bottom and a liquid phase on top. The other culture tested after freezing—is tested in the same manner. The yeast fermentative performance is graded after 90 min from 0 to 5 according to the following score:

Time: Yeast strains that initiate fermentation after 30 min of incubation receive 1 point, while yeast strains that start to ferment after 60 min receive 0.5 point and yeast strains with delayed initiation after 90 min do not receive any point.

Bubbles: Samples without appearance of bubbles in the liquid phase do not receive any points, samples with a small number of bubbles receive 0.5 point, while samples with a lot of bubbles receive 1 point.

Holes: Samples without holes in the solid phase do not receive points. Samples with small holes in it receive 0.5 point and dough with large holes receive 1 point. Samples with large connected holes receive 1.5 points.

Foam: Samples without foam on top of the liquid phase do not receive any points. Samples with a thin foam layer receive 0.5 point, samples with a thick foam layer receive 1 point, and samples with foam layer above 0.5 cm receive 1.5 points Preferably, a yeast strain of the invention is assessed with a fermentative performance score of at least 1, at least 1.5, at least 2 or at least 3 after freezing. More preferably, the decrease in fermentative performance after freezing compared to the fermentative performance before freezing is at most 2 or at most 1.5 or at most 1.

Preferably, a yeast strain obtainable from any of strains OL-01, S3-02, FL-03, IS-310, CC-05 and KF-06, e.g., by breeding between them as described above, demonstrates a fermentative performance after freezing that is lower than the (average) parental fermentative performance in 1 point at most, preferably in 0.5 point at most, preferably equal to the parental strains, and more preferably higher than the parental strains.

Preferably, a yeast strain obtainable from any of strains OL-01, S3-02, FL-03, IS-310, CC-05 and KF-06, e.g., by breeding between them as described above, demonstrates a decrease in fermentative performance after freezing that does not exceed the parental strains' (average) decrease in more than 1 point, preferably, the decrease is equal to the parental strains' decrease or more preferably, lower than the parental strain's decrease. Most preferably, there is no decrease at all.

The baker's yeast strain of the invention advantageously also has excellent fermentative ability. Fermentative ability may be determined following the protocol disclosed in Example 3, if non-frozen dough is used, or, if fermentative ability after freezing is of interest, in Example 4.

Preferably, fermentative ability of a yeast strain of the invention on non-frozen dough is at least comparable (up to +1-20%) to the fermentative ability of commercially available yeast strains such as FTY-3 (BP FERM 2363). A yeast strain of the invention may also have a superior ratio of fermentative ability of sugar dough (in particular, high sugar dough, e.g., 11% sugar or more) to non-sugar dough. The inventors showed that in preferred yeast strains of the invention, e.g., OL-01 or, in particular, CC-05, the fermentative ability on high sugar dough is exceptionally high, which is unique for yeast strains used in frozen dough application, preferably, the ratio of the fermentative ability on 11% sugar dough/fermentative ability on non-sugar dough is at least 1.2, preferably, at least 1.3, at least 1.5, at least 1.7 or at least 1.9. OL-01 was shown to have a particularly high fermentative ability in high sugar dough, and particularly CC-05, may advantageously have high fermentative ability in both lean and high sugar doughs.

With regard to fermentative ability in frozen dough, for example, the strain of the invention may show at least 90%, preferably, at least 91%, at least 93%, at least 95% fermentative ability after storage of dough prepared with said yeast strain at −20° C. for 4 weeks and, preferably, after 8 weeks, compared to its fermentative ability after storage of said dough at −20° C. for 1 day.

Alternatively, or additionally, the strain may show at least 75%, preferably, at least 78% at least 80%, at least 82%, or at least 84% fermentative ability after storage of dough prepared with said yeast strain at −20° C. for 4 weeks with at least 5, at least 10, at least 15, at least 20 or at least 25 freezing/thawing cycles performed during the first 2 weeks of storage (preferably at least 10 freezing/thawing cycles), wherein dough is transferred to 25° C. (e.g., for 30 min) and returned to −20° C. for (e.g., for at least 2 h) one freezing/thawing cycle, compared to its fermentative ability after storage of said dough at −20° C. for 1 day.

The yeast strain of the invention may be capable of fermenting glucose and sucrose, as well as, optionally, maltose, galactose and raffinose. The yeast may be capable of assimilating carbon from glucose and sucrose, as well as, optionally, maltose, galactose and/or raffinose, which can be determined according to the method of Example 2. Typically, melibiose, and optionally, galactose and/or raffinose, cannot be assimilated. The strains of the invention each demonstrate a typical sugar spectrum to assimilate and grow on it.

The invention also provides a yeast product comprising yeast of a baker's yeast strain of the invention, wherein the yeast product is selected from the group comprising compressed yeast, crumbled yeast, cream yeast, active semi dry yeast, dry yeast, such as active dry yeast, instant dry yeast or instant active dry yeast, and frozen yeast. The yeast product may have a solids content of 10-99%.

Cream yeast, also designated liquid yeast, is used mainly by industrial bakeries. The main advantage of this product is that it is delivered directly in chilled containers for bakeries and can be pumped and dosed automatically. Cream yeast should be stored under cooled conditions, and its dry matter content is about 20% (T. Boekhout (Author, Editor), V. Robert (Editor), Yeasts in Food: Beneficial and Detrimental Aspects, Woodhead Publishing Series in Food Science, Technology and Nutrition, 2003, page 297).

Compressed yeast, also designated fresh compressed yeast is produced from the cream yeast. Filtration using a filter press or a rotary vacuum filter is typically used in order to eliminate part of the water contained in the cream yeast. The dry matter of this product varies between 28 and 35%, and depends on the country and the habits of the bakers. Compressed yeast with a lower dry matter content is darker in color and has a kneadable, rather plastic consistency. At high dry matter content the compressed yeast is more whitish and becomes crumbly. Fresh yeast must be preserved under cool conditions, e.g., at temperature of about 4° C. or less, but it may also be frozen. If the cold chain is disturbed and the temperature is raised, the fresh yeast loses its activity rapidly. This product can be produced in different formats, such as small cubes for home baking, blocks of 500 grams or 1 kg and bags of 25 kg. The shelf life of the product is around 5 weeks. (T. Boekhout (Author, Editor), V. Robert (Editor), Yeasts in Food: Beneficial and Detrimental Aspects, Woodhead Publishing Series in Food Science, Technology and Nutrition, 2003, Page 297). Compressed yeast is a preferred yeast of the invention, in particular, for commercial use.

Crumbled yeast is a fresh yeast crumbled into irregular pieces of about 1 cm×5-10 cm before being packed into 25-50 pound bags and stored under refrigeration to ensure stability during storage for about 4 weeks. Despite these precautionary measures, a loss of fermentation activity of 3-5% per week at 5-8° C. is unavoidable, the packaged products may also be frozen. (Byong H. Lee, Fundamentals of Food Biotechnology, 2014, Wiley-Blackwell, page 184).

Active semi dry yeast has a solids content of 70-80% (w/w). It is typically stored at 0-6° C., but it may also be frozen.

Active dry yeast products typically have a solids content of 90 or more % (w/w). All forms of active semi-dry or dry yeast can be stored at room temperature or refrigerated. Freezing is typically not required, even for long-term storage, but is possible. They are preferably packaged in vacuum or in an inert gas (like Nitrogen).

The yeast strains of the invention may also be used for the production of dry yeast products, i.e., active dry yeast (ADY), instant dry yeast (IDY), instant active dry yeast (Instant ADY) and protected active dry yeast (PADY). Compressed cake yeast may be treated with processing aids or antioxidants prior to drying, then extruded to spaghetti-like threads. After braking of the threads to 1.5-3 cm length, they are dried, e.g., in a tunnel on a conveyor belt type of dryer, e.g. fluid bed dryer. This kind of drying produces ADY. In order to activate ADY a separate step for rehydration with water is needed.

Instant ADYs with higher activity than ADYs require gentler drying, which is effected by fluidized-bed or airlift drying processes. The high activity of instant ADY is due to high porosity, there is no need for rehydration and can usually be added directly to dough. PADY contains an emulsifier and is dried by a special process to a moisture level of 5-6%. Use of antioxidants in this product reduces the adverse effect of oxygen and eliminates the need of special packaging. (Karel Kulp, Klaus Lorenz (ed.), Handbook of Dough Fermentations, 2003, CRC Press, ISBN 9780824742645).

The yeast product may be frozen yeast, e.g., frozen active semi dry yeast having 70-85%, in particular, 74-80% (w/w) dry matter, e.g., in the form of dry frozen "noodles". Frozen active semi dry yeast can be directly incorporated into flour without requiring prior thawing. The frozen yeast may also be a frozen active semi dry yeast product having diameter of less than 3 mm and a dry matter content from 70 to 85% (w/w), preferably, 70-80% (w/w) dry matter, as disclosed in EP 1 209 225 A1 and CA 1299435. Frozen yeast can, e.g., be used for preparation of frozen dough. Frozen yeast products are stable for at least four weeks, preferably, at least 8 weeks, at least 12 weeks, at least 3 months, at least 4 months, at least 20 weeks, at least 6 months, at least 1 year, or at least 2 years.

The invention also provides a method for producing a yeast product, comprising culturing the baker's yeast strain of the invention, and, optionally, freezing the yeast.

Yeast products of the invention comprise yeast of a yeast strain of the invention. They may additionally comprise other baker's yeast, i.e., in the form of a mixture of different yeast strains.

The invention also provides a dough or dough product comprising the baker's yeast strain or the yeast product of the invention. The concentration of yeast (for compressed yeast of at least 30% dry matter) employed may be, e.g., 0.5% to 10% (w/w of flour), 1-7% or 2-5%. The concentration is typically comparable or less than concentrations of traditional yeast employed for comparable products. Preferably, in particular, if the yeast and/or the dough or dough product is frozen, a smaller concentration of yeast may be employed, preferably, about 30-90% of classical amounts recommended, 30-85%, 40-80%, 45-75% or 50-70%, without significantly affecting the texture of the obtained baked dough product.

A dough is obtainable by mixing yeast of the invention with at least one ingredient selected from the group comprising flour, and a liquid, with or without the addition of sugar. Typically, yeast is mixed with at least flour and a liquid. Typical ingredients used in dough, as well as suitable concentrations, are well known to the skilled person. The added liquid may be, e.g., water, milk, butter-milk, beer, optionally with the addition of oil. Water and milk powder may be used instead of milk.

Further optional dough ingredients are, e.g., sugar, salt, eggs and/or fat. Preferably, the dough comprises salt. Egg powder may be used instead of fresh eggs. Fat may be, e.g., oil, butter or margarine. The dough may of course also comprise further dough ingredients, such as sourdough or a pre-dough mixture comprising at least one microorganism, spices (e.g., cinnamon, vanilla, pepper, garlic and/or herbs), grated lemon skin, baking improver, enzyme and/or salt. Fruits and/or vegetables, e.g., in dried or mashed form may be additional dough ingredients, e.g., raisins for sweet breads or cakes. In a preferred embodiment, e.g., for bread or rolls, the dough is sourdough.

The dough or dough product may comprise, e.g., 0-40% sugar, in particular, it may be non-sugar dough, lean sugar dough (1-10% sugar), or high sugar dough (more than 10% sugar, preferably, up to 25% or more). The inventors have been able to show that the yeast of the invention have comparable fermentative ability on non-sugar dough and lean sugar dough as commercially available yeast strains, and they, in particular, OL-01, have a particularly high fermentative ability on high sugar dough. The yeast strains of the invention are thus preferably used for high sugar dough, e.g., in particular for frozen high sugar dough. The dough optionally comprises up to 25% fat.

If a frozen yeast product of the invention is used, in particular if said yeast product has a small particle size, thawing is not required for preparation of dough, but the frozen product may be directly added to the dough ingredients, or to at least one other ingredient (e.g., flour). It is however of course possible to first thaw the frozen yeast product at a temperature of 0-37° C., e.g., at temperatures of about 0-8° C., or at room temperature (preferably, 20-25° C.), or at 30-37° C., or with a stepwise increase in the temperatures, e.g., first bringing the temperature to about 0-8° C., and then to room temperature or higher temperatures.

Flour is a powder made by grinding uncooked cereal grains or other seeds or roots. Typically, flour is wheat flour, rye four, spelt flour, maize flour, oat flour, buckwheat flour, gluten-free flour or rice flour, or a mixture thereof, preferably, wheat flour. Flour types may be selected from the group comprising pastry flour, all purpose-flour, strong flour, very strong flour and/or whole-meal flour, or any of the types classified according to mineral content according to DIN 10355, e.g., type 405, type 550, type 650, type 812, type 1050 and/or type 1600. Flour may contain ascorbic acid. It is optionally treated with bleaching and/or maturing agents. If the dough contains sugar, in particular, if it is a high sugar dough, typically, pastry flour (corresponding to type 405) or type 550 flour from wheat is used.

The invention also provides frozen dough or frozen dough products. Frozen describes maintenance at −18° C. or less or −20° C. Dough can be frozen by transferring the dough to a freezer of appropriate temperature, or, preferably, by using methods capable of lowering the temperature of dough more quickly, e.g., using a blast freezer.

In one embodiment, the frozen dough or dough product is obtained by mixing a frozen yeast product of the invention, optionally, after thawing, with at least one of the dough ingredients described above.

In another embodiment, the frozen dough or dough product is obtained by mixing a cream yeast or compressed yeast product of the invention (preferably, a compressed yeast product) with at least one of the dough ingredients described above.

In the context of the invention, a dough product is a formed dough piece. It may be raw, semi-raw (i.e., partly baked) or baked. It may also be frozen, in particular, a raw frozen dough piece. Semi-raw or baked dough pieces may also be frozen, but the yeast's freeze-resistant characteristics are most relevant where raw dough or dough products are frozen. In one embodiment, the dough product is a baked dough product obtained from a frozen dough or, preferably, a frozen dough product of the invention.

The dough or dough product of the invention may be bread dough, roll dough, pizza dough, cake dough, croissant dough, pretzel dough, bagel dough, all preferably already formed, bread, roll, pizza, croissant, pretzel, bagel and cake. Bread may be, e.g., baguette, ciabatta, whole meal bread, mixed bread, rye bread or sweet bread, e.g., yeast plait. Cakes include, e.g., pastries, muffins or cookies.

The invention further provides a method of preparing a dough or dough product of the invention, comprising steps of
 a) mixing the baker's yeast strain of the invention or the yeast product of the invention with at least one ingredient selected from the group comprising flour, and a liquid, such as water or milk, with or without the addition of sugar.

Further dough ingredients, e.g., as specified above, can be added, and a dough is obtained. The mixing step can be mixing of all dough ingredients together. Alternatively, it is step-wise mixing, wherein the yeast is first mixed with one of the ingredients, e.g., flour, or with a liquid and, wherein said liquid preferably has a temperature of 20-37° C. when using active dry yeast and preferably 0-25° C. when using compressed yeast to obtain a first mixture, and, e.g., after 0-30 min, this first mixture is mixed with the other ingredients. The mixing step typically includes kneading of the dough, e.g., for 1-15 min, preferably, 2-10 min. Kneading affects the consistence of dough by contribution to the development of a gluten network. Kneading is typically carried out at room temperature, but the temperature may also be controlled, e.g., at 16° C. to 30° C. and dough temperature may also be controlled, e.g., at 16-37° C. In particular, for preparation of frozen dough, the temperatures are below 25° C., e.g., at about 16-23° C.

The method of preparing a dough or dough product of the invention optionally comprises one or more further steps selected from the group comprising
 b) forming the dough:
 c) proofing the dough;
 d) freezing the dough;
 e) thawing the dough; and/or
 f) baking the dough.

Steps b), c) and d) may be carried out in any order, and repeated proofing steps may be used to achieve an optimal product. If step e) is carried out, it is carried out after step d). Step f) is typically carried out last, but it may be followed by a freezing and, optionally, thawing step.

In the context of the invention, proofing is considered the process wherein yeast converts fermentable sugars present in dough into carbon dioxide and ethanol. This increases the dough volume and affects rheology, e.g., the texture of the resulting product is lighter. Proofing is typically performed at a temperature between 20° C. and 37°, preferably, at room temperature or at about 25° C. An increased humidity is beneficial, preferably, at least 75% or at least 85% relative humidity. The desired characteristics of the product, and accordingly, proofing conditions, depend on the type of product.

As the yeast of the invention has comparable or increased fermentative ability compared to commercially available yeasts, the conditions can be easily optimized by the skilled person.

Proofing the dough, e.g., for 15-90 min, is typically carried out after kneading. The dough may be formed before proofing. However, typically, after a proofing step, the dough is re-worked, or punched, and, optionally formed. This may be followed by another proofing step, e.g., of 15-90 min.

A raw or frozen dough product may have undergone no proofing, full or partial proofing. Accordingly, freezing may be carried out after kneading, after a partial proofing period (typically, after forming), or after the full (maximum) required proofing. Preferably, freezing is performed after the full required proofing period. Throughout the invention, for convenience reasons, it is preferred that a formed dough product is frozen rather than the unformed dough.

In a preferred embodiment, for non-proofed frozen dough products, dough products are frozen after forming. After thawing, they can be proofed, followed by baking.

In another preferred embodiment, for proofed or at least partially proofed frozen dough products, dough products are formed, proofed (for about 60-100%, typically, about 70-80% of the typical full required proofing volume), and frozen. After thawing and, optionally, further proofing, they may be baked.

After freezing, the dough or dough product may be thawed before baking (at 0° C.-37° C., preferably, at 20° C. to 32° C.), and, optionally, a proofing step may be performed. This may be particularly useful for heavy doughs such as dough containing sugar and/or fat. However, using the yeast of the invention, this is not required, i.e., the dough or dough product may be a frozen dough or dough product suitable for baking without thawing, e.g., a frozen dough in the shape of a baguette.

Advantageously, a frozen dough or dough product of the invention is stable for at least 2 weeks, at least 4 weeks, at least 8 weeks, at least 3 months, at least 6 months or at least a year when frozen at temperatures of −18° C. Stable in the context of the invention means that the product is still appropriate for human consumption, and maintains at least comparable characteristics as a corresponding fresh product.

At any time after forming, e.g., after forming, after proofing, after freezing, after thawing or after baking, additional finishing steps may be performed, e.g., adding toppings such as icing, glazing with egg yolk, milk, sugar, marmalade, or a mixture thereof, or fruit.

The dough product of the invention may also be a baked product. Baking may take place with or without steaming, e.g., at temperatures of about 160-220° C. for times of 15-60 min. Conditions such as temperature and baking time depend on the product (e.g., dough type and size, desired crust) and can easily be determined by the skilled person. In the context of the invention, while baking typically takes place in an oven, baking is understood to include other ways of heating the dough product to temperatures inactivating the yeast, e.g., steaming, heating by microwave, frying, roasting and/or cooking.

The dough or dough product of the invention may also be packaged, e.g., in a can or a foil. Packaging may be under vacuum conditions or in modified atmosphere, preferably, with reduced oxygen content or in the absence of oxygen. The package may include instructions for producing a ready to eat dough product, e.g., for further steps of dough preparation and baking.

For example, a frozen dough product may be obtainable by mixing the ingredients, kneading, proofing the dough (e.g., for 15-30 min at room temperature, preferably about 25° C., re-working and forming the dough, optionally, further proofing the dough at room temperature, preferably about 25° C., for 15-45 min, e.g., 30-40 min, and freezing (e.g., at −18° to −20° C.). Before baking, the frozen dough product may be thawed (e.g., at 32° C., 75% relative humidity) for at least 5 or at least 10 min, such as for about 30-45 min. Preferably, thawing is sufficient to obtain a dough consistency which assures maximum volume of the product. The dough product may however also be directly baked out of the freezer, without thawing.

The invention also provides use of the baker's yeast strain of the invention or the yeast product of the invention for preparing a dough or dough product, wherein the dough or dough product may be a frozen dough or dough product.

The invention is further described in the following examples to illustrate the invention, but the examples are not intended to limit the scope of the invention. All references cited herein are herewith fully incorporated herein for all purposes.

FIG. 1 Survival rate of yeast strains of the invention compared with state of the art commercial yeast strains. Saccharomyces cerevisiae strains OL-01, S3-02, FL-03, IS-310, CC-05, KF-06, commercial baker's yeast strain for frozen dough and freeze resistant strain FTY-3 (FERM BP 2363 (US 5,352,606 B1)) were grown on YPD medium, harvested and re-suspended in fresh YPD medium to a concentration of 5 $OD_{600}$. Yeast suspensions were incubated in −20° C. for 48-72 hours, followed by four freezing/thawing cycles (1.5 h in 30° C./at least 1 h in −20° C.). Viable yeast counts were measured using seeding decimal dilutions of yeast suspensions on YPD agar plates and incubation in 30° C. for 48 hours. Survival rate was determined as follows:

Survival rate=Final number of yeast colonies/Initial number of yeast colonies×100%

Figure 2:
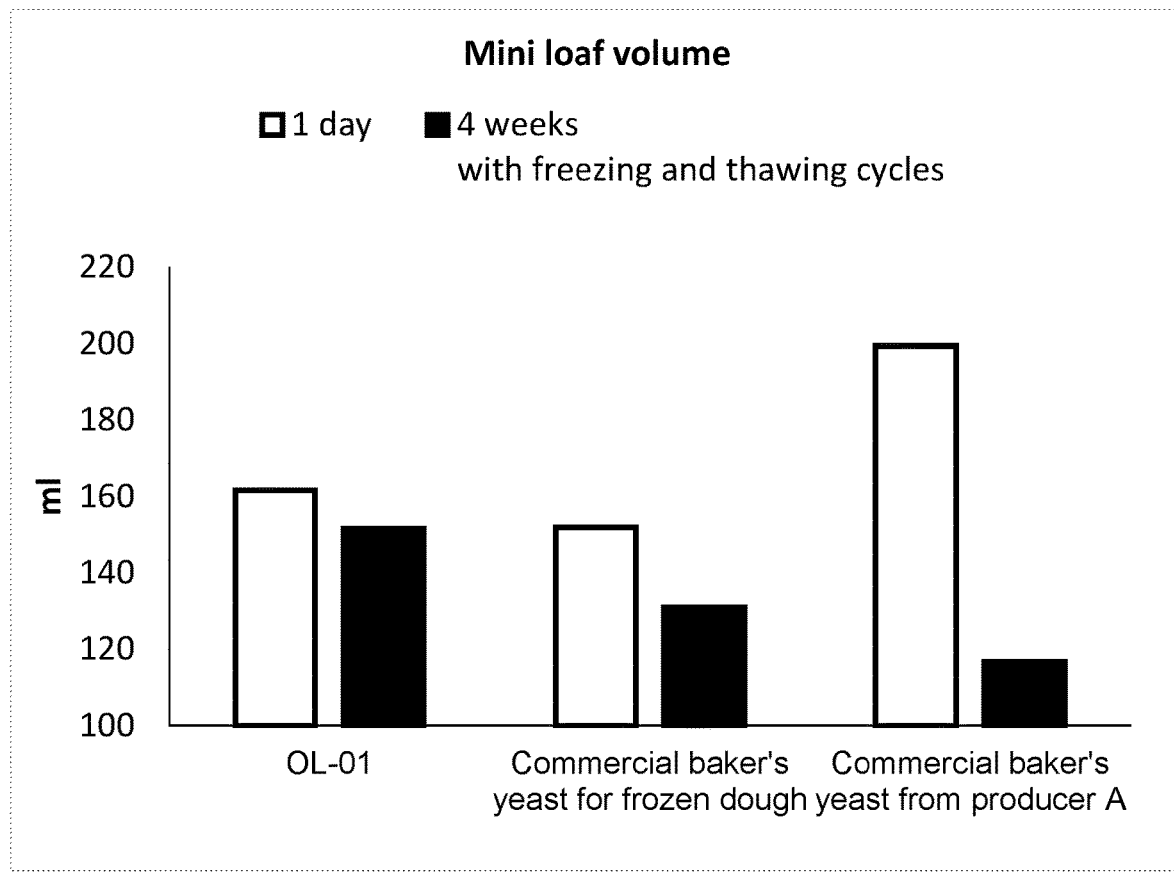
FIG. 2 Mini loaf volume of frozen no sugar dough samples of yeast strain of the invention compared with state of the art commercial yeast strains.

FIG. 2 Mini loaf volume of frozen no sugar dough samples of yeast strain of the invention compared with state of the art commercial yeast strains. Saccharomyces cerevisiae strain OL-01 culture obtained as described in Example 3, commercial baker's yeast for frozen dough and commercial baker's yeast for all purposes dough applications were used for preparation of non-sugar dough. Dough was prepared, divided to portions of 50 g, molded, and frozen to −20° C. using a blast freezer, transferred to a polyethylene bag and then stored in a −20° C. freezer for a period of up to 4 weeks. On one day storage at −20° C. and 4 weeks storage at −20° C. with freezing/thawing cycles after preparation, dough samples were thawed at 25° C. for 20-30 min, proofed and baked in mini loaf pans. Mini loafs apparent volume was measured after cooling to room temperature according to a solids displacement method used to measure the volume of irregular solids (Physical Properties of Foods, Serpil Sahin, Servet Gulum Sumnu, page 20) using poppy seeds.

Figure 3:
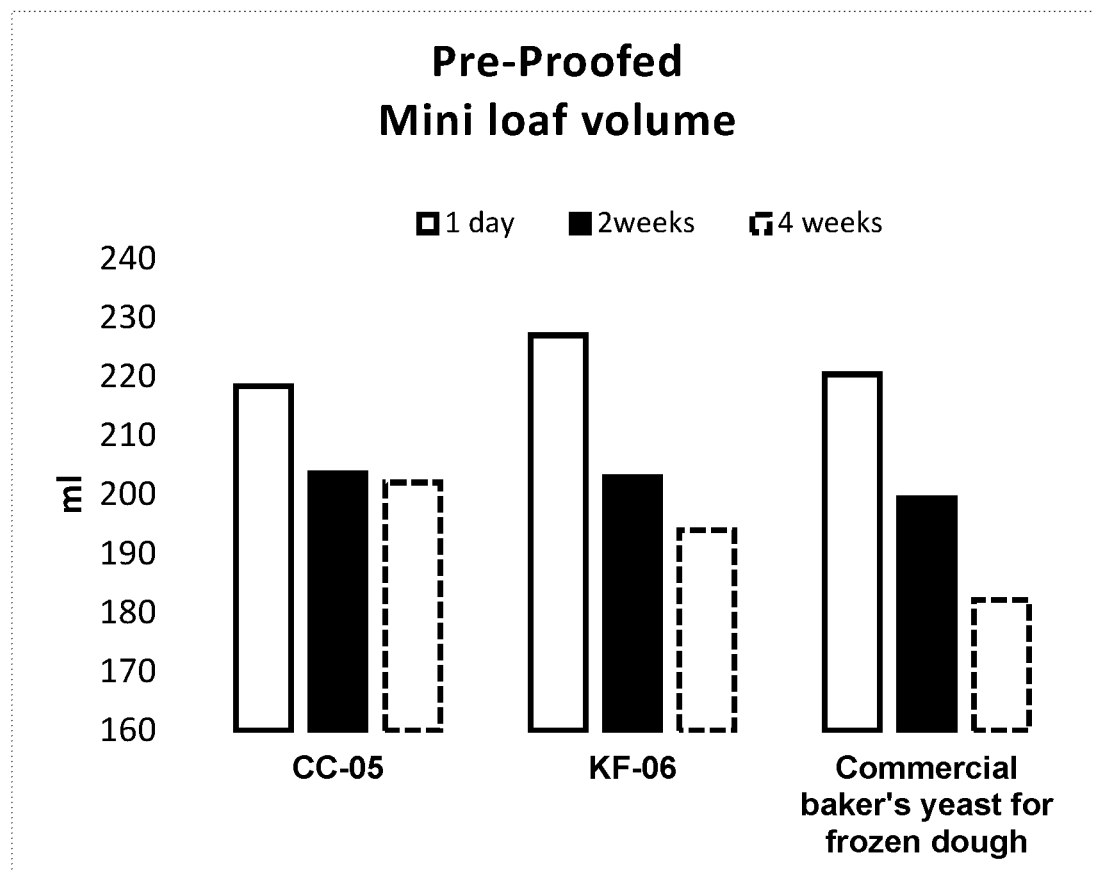
FIG. 3 Mini loaf volume of pre-proofed dough samples of yeast strain of the invention compared with state of the art commercial yeast strains.

FIG. 3 Mini loaf volume of pre-proofed dough samples of yeast strain of the invention compared with state of the art commercial yeast strains. Non-sugar dough samples (50-80 g) obtained as in Example 4.2 after 1 day storage at −20° C. and after 4 weeks storage at −20° C. frozen pre-proofed mini loafs were directly baked, with no thawing stage, as described in Example 7.2. The mini loafs' apparent volume was measured after cooling to room temperature according to a solids displacement method used to measure the volume of irregular solids (Physical Properties of Foods, Serpil Sahin, Servet Gulum Sumnu, page 20) using poppy seeds.

EXAMPLES

Example 1

New Yeast Strains and Their Morphology

New freeze-resistant Saccharomyces cerevisiae strains OL-01 (NCYC 4095), S3-02 (NCYC 4094), FL-03 (NCYC 4105), IS-310 (NCYC 4106), CC-05 (NCYC 4128) and KF-06 (NCYC 4129) were selected and deposited in NCYC under the Budapest Treaty. FL-03 and IS-310 were obtained by breeding of offspring of OL-01 and S3-02. CC-05 was obtained by breeding comprising offspring of OL-01 and S3-02.

Each yeast strain was propagated in YPD medium (cf. Table 2) and observed under a microscope for morphological characteristics. Yeast colonies were grown on YPD-agar (cf. Table 2) and observed for their morphological properties.

Sporulation: yeast grown on YPD-agar plates was further seeded on SPO agar plates (cf. Table 2) and incubated at 25° C. for 7-10 days. Occurrence of sporulation was confirmed by microscope observation.

TABLE 1

Morphological properties of the new yeast strains

|  | O1-01 | S3-02 | FL-03 | IS-310 | CC-05 | KF-06 |
|---|---|---|---|---|---|---|
| *Characteristic of the yeast cell* | | | | | | |
| Shape | Round | Round | Round | Round | Round | Round |
| Size (μm) | 4.4 | 5.3 | 5.7 | 5.2 | 5.2 | 5.0 |
| Sporulation | + | + | + | + | + | + |
| Budding | + | + | + | + | + | + |
| Film formation | − | − | − | − | − | − |
| Aggregation | − | + | + | + | ± | ± |
| *Characteristic of yeast's colony* | | | | | | |
| Form | Circular | Circular | Circular | Circular | Circular | Circular |
| *Characteristic of the yeast cell* | | | | | | |
| Surface | Smooth | Smooth | Smooth | Smooth | Smooth | Smooth |
| Elevation | Raised | Raised | Raised | Raised | Raised | Raised |
| Margin | Entire | Entire | Entire | Entire | Entire | Entire |
| Size | Medium | Medium | Medium | Medium | Medium | Medium |
| Optic | Opaque | Opaque | Opaque | Opaque | Opaque | Opaque |
| Color | White | White | White | White | White | White |
| Agar penetration | — | — | — | — | — | — |

TABLE 2

Media composition

|  | YPD | YPD agar | SPO agar | YNB |
|---|---|---|---|---|
| Glucose (g) | 20 | 20 | 0.5 | — |
| Yeast extract (g) | 10 | 10 | 1 | — |
| Peptone (g) | 20 | 20 | — | — |
| Agar (g) | — | 20 | 20 | 20 |
| $KH_2PO_4$ (g) | — | — | — | 4 |
| $MgSO_4 \cdot 7H_2O$ (g) | — | — | — | 0.4 |
| $(NH_4)_2SO_4$ (g) | — | — | — | 5 |
| Yeast nitrogen base (g) | — | — | — | 10 |
| $KCH_3COO$ (g) | — | — | 10 | — |
| Distilled water (mL) | 1000 | 1000 | 1000 | 1000 |

Further freeze-resistant yeast strains of the invention may be obtained by breeding between any of OL-01, S3-02, FL-03, IS-310, CC-05 and KF-06.

The freeze tolerance yeast strains can be obtained by conventional non GMO yeast improvement methods such as random mutagenesis, and breeding methods including: sexual recombination, and genome shuffling. These methods are detailed in two review articles: Giudici P. Solieri L. Pulvirenti A M. Cassanelli S. 2005 Appl Microbiol Biotechnol 66: 622-628. Steensels J. Snoek T., Meersman E, Nicolino M. P., Voordeckers K. M & Verstrepen K. J. 2014 FEMS Microbiol Rev 38 947-995.

Said yeast can be obtained by random mutagenesis using mutagens (for instant chemical mutagen or UV) to generate genetic diversity in yeast population followed by selection toward a desired trait as described in Matsutani, K., Y. Fukuda, K. Murata, A. Kimura, I. Nakamura, and N. Yajima. 1990. J. Ferment. Bioeng.70:275-276.

Alternatively, using sexual recombination that includes breeding of yeast strains usually involves one of the following approaches: single-spore culture grown after germination as described in Nakagawa, S. and Ouchi, K. 1994 Appl. Environ. Microbiol. 60,3499-3502, and random gamets as described in Giudici P. Solieri L. Pulvirenti A M. Cassanelli S. 2005 Appl Microbiol Biotechnol 66: 622-628.

Moreover, said yeast can be obtained using genome shuffling method, conducted by repetitive recombination between numerous parents followed by screening, as described in Paolo Giudici. Lisa Solieri. Andrea M. Pulvirenti. Stefano Cassanelli 2005 Appl Microbiol Biotechnol 66: 622-628.

A screening method for freeze-resistance can facilitate each of the breeding methods. It is possible to test the strains for freeze resistance by testing their viability after repeated freeze-thaw cycles (up to 200) in dough or after freezing in YPD media as described in Teunissen A, et al. 2002. Applied and Environmental Microbiology 68: 4780-4787 and in Tanghe A, et al., 2002. Applied and Environmental Microbiology 68 5981-5989.

Example 2

Carbon Source Assimilation

Carbohydrates assimilation was analyzed as follows. *Saccharomyces cerevisiae* strains OL-01, S3-02, FL-03, IS-310, CC-05 and KF-06 were grown on YPD medium for 15 hours with agitating (200 rpm), harvested and washed twice with sterilized water by centrifugation and re-suspended to a concentration of 0.5 OD/ml in YNB medium with various carbohydrates (2% w/v) respectively. The suspensions were incubated at 30° C. with agitation of 200 rpm for 18 hours (OL-01, S3-02, FL-03, IS-310) or at 37° C. with agitation of 100 rpm for 20 hours (CC-05, KF-06). Turbidity of the cultures was measured by absorbance at 600 nm, to confirm yeast growth after 13 hours and after 18 hours. Estimation of growth ability was calculated in comparison to growth on glucose and without any sugar. Sugar types with which the yeast strain reached at least 80% of its concentration compared with growth on glucose was scored with "+". Sugar types with which the yeast strain reached more than 20% above its concentration compared with growth without any sugar and less than 80% of its concentration compared to growth on glucose scored "±". Sugar types with which the yeast strain con-centration not exceed in more than 20% on its concentration without any sugar, scored "−".

TABLE 3

Carbon source assimilation of new yeast strains

|  | OL-01 | S3-02 | FL-03 | IS-310 | CC-05 | KF-06 |
|---|---|---|---|---|---|---|
| Glucose | + | + | + | + | + | + |
| Sucrose | + | + | + | + | + | + |
| Maltose | ± | + | + | + | + | ± |
| Galactose | ± | ± | ± | ± | + | + |
| Raffinose | ± | ± | ± | ± | NA | NA |
| Melibiose | − | − | − | − | − | − |

This experiment shows that yeast of invention demonstrates a typical carbon assimilation pattern.

Example 3

Fermentative Ability of Non-Frozen Dough 3.1 Culturing the Novel *Saccharomyces cerevisiae* Strains.

A loopfull of fresh yeast was transferred from YPD agar plate to a 250 ml Erlenmeyer flask containing 60 mL molasses 12.5° Bx (Brix) and incubated in a shaker incubator at 30° C. with agitation of 200 rpm for 24 hours. Twenty mL of obtained yeast suspension were aseptically transferred into 1L Erlenmeyer flask containing 105 mL molasses 12.5° Bx and incubated under the same conditions for 48h, to produce seed yeast for main fermentation in a 5 L fermenter.

The culture solution was then inoculated into a 7 L fermenter vessel containing 2.5 L molasses medium (see Table 4) and grown under the conditions shown in Table 44 to obtain seed yeast for a 5 L fermenter culture.

The main culture medium shown in Table 4 was prepared in a volume of 5 L in a 7 L fermenter vessel and inoculated with the whole volume of the seed culture grown in a 2.5 L molasses medium in a 7 L fermenter, followed by culture under the following conditions.

TABLE 4

Fermentation conditions

| Ingredient | 2.5 L seed culture Batch | 5 L main culture Fed batch |
|---|---|---|
| Inoculum | 125 mL | 185 mL |
| Deionized water | 2125 mL | 3700 mL |
| Beat & Cane molasses (optionally between 20 to 100% cane molasses) | 235 mL~43° Bx | 818 mL~50° Bx |
| Ammonia source | 12.5 mL (NH$_4$)$_2$SO$_4$ 20% | 107 mL Ammonia 11% |
| H$_3$PO$_4$ (85%) | 0.3 mL | 1.75 mL |
| MgSO$_4$ 7H$_2$O | 0.25 g | 0.5 g |
| Biotin | 1.5 mg | 3 mg |
| Thiamine | 6.25 mg | 12.5 mg |
| Pantothenic acid | 5 mg | 10 mg |
| Cultured conditions | | |
| Temperature | 30-32° C. | 30-32° C. |
| Aeration volume | 0.8 vvm | 1.6-2 vvm |
| Agitation | 200-600 rpm | 900-1000 rpm |
| Ph | 5.0-5.5 | 5.0-5.5 |
| Culturing time | 10 hr | 12 hr |

After completion of fermentation, yeast's cells were washed with sterile water and separated by centrifugation followed by re-suspension in water to obtain yeast cream (18-23% dry matter) or separated by centrifugation and filtration to obtain compressed yeast with 28-35% dry matter.

The fermentation procedure described above is described, e.g., in Yeast Strain Selection edited by Chandra J. Panchal, 1990, page 140, which is incorporated by reference, or in U.S. Pat. Nos. 4,232,045, 3,617,306A, EP 0 237 427 B2, the entire disclosures of which are also incorporated by reference.

3.2. Fermentative Ability on Non-Frozen Dough 3.2.1 Two types of dough samples were prepared for each yeast sample according to the composition described in Table 5 using white wheat flour Type 550 (German specification, i.e., ash content 0.50-0.58%, extraction rate ~72%, gluten content of 9-11%). Immediately after preparation, dough samples were analyzed for fermentative ability using the ANKOM$^{RF}$ Gas Production Measurement System (K. Müller-Auffermann et al, 2014. Brewing Science 67:72-80). The measurements were carried out in 30° C. for 60 minutes. This system determines baker's yeast CO$_2$ production levels in terms of pressure and temperature converted to CO$_2$ volume. Table 6 shows the results obtained.

TABLE 5

Dough composition

| | Sugar [% w/w of flour] | Salt [% w/w of flour] | Yeast (30% solids) [% w/w of flour] | Fat [% w/w of flour] | Water [% w/w of flour] |
|---|---|---|---|---|---|
| Non sugar dough | 0 | 1.4 | 2 | 0 | 54 |
| 11% sugar dough | 11 | 1.2 | 6 | 15 | 40 |

TABLE 6

Fermentative ability (ml CO$_2$) on non-frozen (fresh) doughs

| | Non sugar dough [ml CO$_2$/hr/100 gr dough] | 11% sugar dough [ml CO$_2$/hr/100 gr dough] | Fermentative ability on 11% sugar dough/ fermentative ability on non sugar dough |
|---|---|---|---|
| OL-01 | 93 | 176 | 1.9 |
| S3-02 | 106 | 124 | 1.2 |
| IS-310 | 96 | 127 | 1.3 |
| CC-05 | 96 | 161 | 1.7 |
| KF-06 | 86 | 137 | 1.6 |
| FTY-3 (BP FERM 2363) strain | 104 | 86 | 0.8 |
| Commercial baker's yeast used in frozen dough | 94 | 119 | 1.3 |
| Commercial baker's yeast from producer A | 127 | 161 | 1.3 |
| Commercial baker's yeast from producer B | 106 | 120 | 1.1 |
| Commercial baker's yeast from producer C | 110 | 125 | 1.1 |

3.2.2 Two types of dough samples were prepared for each yeast sample according to the composition described in Table 7 using a bright white wheat flour, ash content ~0.4%, protein ~11%, wet gluten content of ~29%.

Immediately after preparation, dough samples were analyzed for fermentative ability using the ANKOM$^{RF}$ Gas Production Measurement System (K. Muller-Auffermann et al, 2014. Brewing Science 67:72-80). The measurements were carried out in 37° C. for 60 minutes. This system determines baker's yeast CO$_2$ production levels in terms of pressure and temperature converted to CO$_2$ volume. Table 8 shows the results obtained.

TABLE 7

Dough composition

|  | Sugar [% w/w of flour] | Salt [% w/w of flour] | Yeast (30% solids) [% w/w of flour] | Water [% w/w of flour] |
|---|---|---|---|---|
| 2% sugar dough | 2 | 1.5 | 4 | 62 |
| 15% sugar dough | 15 | 1.5 | 4 | 53 |

TABLE 8

Fermentative ability (ml $CO_2$) on non-frozen (fresh) doughs

|  | 2% sugar dough [ml $CO_2$] | 15% sugar dough [ml $CO_2$] |
|---|---|---|
| OL-01 | 329 | 182 |
| S3-02 | 350 | 168 |
| Commercial baker's yeast used in frozen dough | 310 | 148 |
| Commercial baker's yeast from producer A | 382 | 190 |
| Commercial baker's yeast from producer B | 318 | 134 |

3.2.3 Two types of dough samples were prepared for each yeast sample according to the composition described in Table 9 using a bright white wheat flour, protein ~11%, wet gluten content of ~32%.

Immediately after preparation, dough samples were analyzed for fermentative ability using the ANKOM$^{RF}$ Gas Production Measurement System (K. Müller-Auffermann et al, 2014. Brewing Science 67:72-80). The measurements were carried out at 28° C. for 60 minutes. This system determines baker's yeast $CO_2$ production levels in terms of pressure and temperature converted to $CO_2$ volume. Table 10 shows the results obtained.

TABLE 9

Dough composition

|  | Sugar [% w/w of flour] | Salt [% w/w of flour] | Yeast (20% solids) [% w/w of flour] | Water [% w/w of flour] |
|---|---|---|---|---|
| 0% sugar dough | 0 | 2 | 4.8 | 57 |
| 16% sugar dough | 16 | 2 | 8 | 53 |

TABLE 10

Fermentative ability (ml $CO_2$) on non-frozen (fresh) doughs

|  | Non sugar dough [ml $CO_2$/90 min/100 gr dough] | 16% sugar dough [ml $CO_2$/hr/100 gr dough] | Decrease in fermentative activity in 16% sugar dough compared to non-sugar dough |
|---|---|---|---|
| CC-05 | 158 | 130 | −17% |
| Commercial baker's yeast used in frozen dough | 160 | 103 | −36% |

Experiments 3.2.1, 3.2.2, and 3.2.3 show that the tested novel strains show at least comparative fermentative ability to commercially available yeast strains on fresh, non-frozen dough. In preferred yeast strains of the invention, the fermentative ability on high sugar dough is exceptionally high, which is unique for yeast strains for application in frozen dough, preferably, the ratio of the fermentative ability on 11% sugar dough/fermentative ability on non sugar dough is at least 1.2, preferably, at least 1.3, at least 1.5, at least 1.7 or at least 1.9. Preferably, the decrease in fermentative activity in 16% sugar dough compared to non-sugar dough is at least less than 30%, preferably less than 25%, preferably less than 20%, and more preferably equal or less than 17%. OL-01 was shown to have a particularly high fermentative ability in high sugar dough. The experiment shows that the novel yeast strains of the invention, and particularly CC-05, may advantageously have high fermentative ability in both lean and high sugar doughs.

Example 4

Fermentative Ability on Frozen Dough 4.1 No Sugar, Frozen Dough:

4.1.1 Yeast cultures obtained in Example 3 and commercial yeast products were used for preparation of non-sugar dough containing about 2% (w/w of flour) salt, 4% (w/w of flour) yeast (30% solids), 53% (w/w of flour) of water using a bright white wheat flour. Dough was prepared, divided to portions of 50 g, molded, and frozen to −20° C. using a blast freezer, transferred to a polyethylene bag and then stored in a −20° C. freezer for a period of up to 4 weeks. One day and 4 weeks after preparation, dough samples were thawed at 25° C. for 20-30 min and tested for $CO_2$ release during 90 min incubation at 37° C., using the ANKOM$^{RF}$ Gas Production Measurement System. This method determines baker's yeast $CO_2$ production levels in terms of pressure and temperature that are further converted to $CO_2$ volume. The measurements were carried out, and the total gas volume of 1 day and 4 weeks storage at −20° C. samples was measured. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least two hours for one freezing/thawing cycle. Table 11 shows the results obtained.

TABLE 11

Persistence of fermentative ability after 4 weeks of freezing presented as % from 1 day measurement

|  | 4 weeks storage | 4 weeks storage with freezing/thawing cycles |
|---|---|---|
| OL-01 | 93% | 84% |
| S3-02 | 93% | 79% |
| IS-310 | 91% | 77% |
| KF-06 | 97% | 86% |
| CC-05 | 98% | 78% |
| Commercial baker's yeast used in frozen dough | 86% | 69% |
| Commercial baker's yeast from producer A | 79% | 47% |
| Commercial baker's yeast from producer B | 70% | 59% |

The experiment shows that the novel yeast strains of the invention may advantageously tolerate long term frozen storage, optionally with multiple freezing/thawing cycles better than commercially available yeast strains, e.g., showing at least 90%, preferably, at least 91% preferably, at least 93% or at least 97% fermentative ability after 4 weeks storage at −20° C. of the fermentative ability after 1 day of storage at −20° C., and at least 70%, at least 73%, preferably, at least 75%, at least 78%, at least 80% or at least 84% fermentative ability after 4 weeks storage at −20° C. with freezing/thawing cycles of the fermentative ability after 1 day of storage at −20° C.

4.1.2 No sugar dough samples (50 g) obtained as in Example 4.1.1 and stored at −20° C. for a period of up to 12 weeks. Dough samples were thawed at 25° C. for 20-30 min and tested for $CO_2$ release during 60 min incubation at 37° C., using the ANKOM$^{RF}$ Gas Production Measurement System. The measurements were carried out, and the total gas volume produced after 1 day, after 8 weeks and after 12 weeks storage at −20° C. was measured. Table 12A shows the results obtained.

In a separate experiment, non-sugar dough samples (50 g) obtained as in Example 4.1.1, stored at −20° C. for a period of up to 24 weeks. Dough samples were thawed at 25° C. for 20-30 min and tested for $CO_2$ release during 90 min incubation at 37° C., using the ANKOM$^{RF}$ Gas Production Measurement System. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least two hours for one freezing/thawing cycle. Table 12B shows the results obtained.

TABLE 12A

Persistence of fermentative ability after 8 and 12 weeks of freezing presented as % from 1 day measurement

| | 8 weeks storage | 12 weeks storage |
|---|---|---|
| OL-01 | 92% | 89% |
| KF-06 | 92% | 80% |
| CC-05 | 93% | 77% |
| Commercial baker's yeast used in frozen dough | 75% | 65% |
| Commercial baker's yeast from producer A | 59% | 31% |

TABLE 12B

Persistence of fermentative ability after 4, 8 and 24 weeks of freezing presented as % from 1 day measurement

| | | % from day 1 | | | |
|---|---|---|---|---|---|
| Yeast strain | Day 1 (ml $CO_2$) | 4 weeks | 4 weeks with freezing/ thawing | 8 weeks | 24 weeks |
| CC-05 | 233 | 96% | 89% | 90% | 72% |
| Commercial baker's yeast used in frozen dough | 227 | 92% | 73% | 85% | 56% |

The experiment shows that the novel yeast strains of the invention may advantageously tolerate long term frozen storage better than commercially available yeast strains, e.g., showing at least 77%, at least 80%, preferably, at least 83%, at least 87% or at least 90% fermentative ability after 8 and 12 weeks storage at −20° C. of the fermentative ability after 1 day of storage at −20° C. Alternatively or additionally, the yeast strains of the invention show at least 60%, preferably, at least 65%, at least 70% or at least 72% fermentative ability after 24 weeks storage at −20° C. of the fermentative ability after 1 day of storage at −20° C.

4.2 No Sugar, Pre Proofed Frozen Dough:

4.2.1 Yeast cultures obtained in Example 3 and commercial yeast product were used for preparation of non-sugar dough containing about 1.5% (w/w of flour) salt, 2% (w/w of flour) yeast (30% solids), 65% (w/w of flour) of water using a bright white wheat flour.

Dough was prepared, divided to portions of 50 g, molded, proofed for 1 hr in a proofing chamber at 30° C. and then frozen to −20° C. using a blast freezer, transferred to a polyethylene bag and then stored in a −20° C. freezer for a period of up to 4 weeks. One day, 2 weeks and 4 weeks after preparation, dough samples were thawed at 25° C. for 20-30 min and tested for $CO_2$ release during 60 min incubation at 37° C., using the ANKOM$^{RF}$ Gas Production Measurement System. The measurements were carried out, and the total gas volume produced after 1 day, after 2 weeks and after 4 weeks storage at −20° C. was measured. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least 2 h for one freezing/thawing cycle. Table 13A shows the results obtained.

TABLE 13A

Persistence of fermentative ability after 2 and 4 weeks of Pre-proofed dough freezing presented as % from 1 day measurement using 2% yeast (30% solids)

| | 2 weeks storage | 2 weeks storage with freezing/ thawing cycles | 4 weeks storage | 4 weeks storage with freezing/ thawing cycles |
|---|---|---|---|---|
| OL-01 | 98% | 80% | 80% | 70% |
| FTY-3 (BP FERM 2363) strain | 72% | 55% | 65% | 44% |
| Commercial baker's yeast used in frozen dough | 65% | 56% | 62% | 42% |

In an alternative setting, Yeast cultures obtained in Example 3 and commercial yeast product were used for preparation of non-sugar dough containing about 1% rapeseed oil (w/w of flour), 2.5% (w/w of flour) salt, 5% (w/w of flour) yeast (30% solids), 56% (w/w of flour) of water using a bright white wheat flour.

Dough was prepared, divided to portions of 80 g, molded, proofed for 70 min at 20° C. and then frozen to −20° C. using a blast freezer transferred to a polyethylene bag and then stored in a −20° C. freezer for a period of up to 2 weeks. One day and 2 weeks after preparation, dough samples were thawed at 25° C. for 20-30 min and tested for $CO_2$ release during 60 min incubation at 37° C., using the ANKOM$^{RF}$ Gas Production Measurement System. The measurements were carried out, and the total gas volume produced after 1 day and after 4 weeks storage at −20° C. was measured. Table 13B shows the results obtained.

TABLE 13B

Persistence of fermentative ability after four weeks of Pre-proofed dough freezing presented as % from 1 day measurement using 5% yeast (30% solids)

| | Day 1 (ml $CO_2$) | 4 weeks storage |
|---|---|---|
| KF-06 | 157 | 97% |
| CC-05 | 132 | 100% |
| Commercial baker's yeast used in frozen dough | 114 | 69% |

4.2.2 Long storage of pre-proofed dough samples. Yeast cultures obtained in Example 3 and commercial yeast product were used for preparation of non-sugar dough containing about 1% rapeseed oil (w/w of flour), 2.5% (w/w of flour) salt, 5% (w/w of flour) yeast (30% solids), 56% (w/w of flour) of water using a bright white wheat flour.

Dough was prepared, divided to portions of 80 g, molded, proofed for 70 min at 20° C. and then frozen to −20° C. using a blast freezer transferred to a polyethylene bag and then stored in a −20° C. freezer for a period of up to 20 weeks. One day, 12 and 20 weeks after preparation, dough samples were thawed at 25° C. for 20-30 min and tested for $CO_2$ release during 90 min incubation at 37° C., using the ANKOM$^{RF}$ Gas Production Measurement System. The measurements were carried out, and the total gas volume produced after 1 day and after 4 weeks storage at −20° C. was measured. The results obtained in this experiment were summarized in Table 14.

TABLE 14

Persistence of fermentative ability after 12 and 20 weeks of Pre-proofed dough freezing presented as % from 1 day measurement using 5% yeast (30% solids)

| | Day 1 | % from day 1 | |
|---|---|---|---|
| Yeast strain | (ml CO2) | 12 weeks | 20 weeks |
| CC-05 | 246 | 80% | 65% |
| Commercial baker's yeast used in frozen dough | 224 | 63% | 50% |

The experiment shows that the novel yeast strains of the invention may advantageously tolerate long term frozen storage of pre-proofed frozen non-sugar dough, optionally with multiple freezing/thawing cycles better than commercially available yeast strains, e.g., showing at least 94%, preferably, at least 95%, or, at least 98% fermentative ability after 2 weeks storage at −20° C. of the fermentative ability after 1 day of storage at −20° C., and at least 65%, preferably, at least 70%, or, at least 75% fermentative ability after 2 weeks storage at −20° C. with freezing/thawing cycles of the fermentative ability after 1 day of storage at −20° C. Also, novel yeast strains preferably demonstrate at least 70%, preferable 80%, or at least 90% fermentative ability after 4 weeks storage of pre-proofed frozen non-sugar dough at −20° C. of the fermentative ability after 1 day of storage at −20° C. The said strains also preferably demonstrate at least 70%, preferable at least 75%, or at least 80% fermentative ability after 12 weeks storage of pre-proofed frozen non-sugar dough at −20° C. of the fermentative ability after 1 day of storage at −20° C.; and at least 55%, preferable 60%, or at least 65% fermentative ability after 20 weeks storage at −20° C. of the fermentative ability after 1 day of storage at −20° C.

4.3 1% Sugar, Pre Proofed Frozen Dough:

Yeast cultures obtained in Example 3 and commercial yeast product were used for preparation of lean sugar doughs containing about 1% (w/w of flour) sugar, 2% (w/w of flour) salt, 5% (w/w of flour) yeast (30% solids), 1% (w/w of flour) rapeseed oil, 56% (w/w of flour) of water using a bright white wheat flour.

Dough was prepared, divided to portions of 70 g, molded, proofed for 40 minutes at room temperature, and then placed in −20° C. freezer. Frozen pre-proofed dough samples were transferred to a polyethylene bag and then stored in a −20° C. freezer for a period of up to 8 weeks. One day, 4 weeks and 8 weeks after preparation, dough samples were thawed at 32° C., about 75% relative humidity for 30-35 min and tested for $CO_2$ release during 90 min incubation at 37° C., using the ANKOM$^{RF}$ Gas Production Measurement System. The measurements were carried out, and the total gas volume produced after 1 day, after 4 weeks and after 8 weeks storage at −20° C. was measured. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least 2 h one freezing/thawing cycle. Table 15A shows the results obtained.

TABLE 15A

Persistence of fermentative ability after 1 day, 4 weeks and 8 weeks of 1% sugar Pre-proofed dough freezing using 5% yeast (30% solids)

| | 1 day storage | 4 weeks storage with freezing/ thawing cycles | 8 weeks storage | 4 weeks storage with freezing/ thawing cycles | 8 weeks storage |
|---|---|---|---|---|---|
| | [ml $CO_2$/hr/50 gr dough] | | | % from 1 day storage | |
| OL-01 | 149 | 148 | 105 | 99% | 70% |
| IS-310 | 183 | 181 | 147 | 99% | 80% |
| Commercial baker's yeast from producer A | 210 | 121 | 93 | 57% | 44% |

In an alternative test, yeast cultures obtained in Example 3 and a commercial yeast product were used for preparation of lean sugar dough containing about 1% (w/w of flour) sugar, 2% (w/w of flour) salt, 7% (w/w of flour) yeast (30% solids), 1% (w/w of flour) butter, 56% (w/w of flour) of water using a bright white wheat flour.

Dough was prepared, divided to portions of 70 g, molded, proofed in a proofing chamber for 10 min at 35° C. and 10 min at room temperature, and then placed in a blast freezer. Frozen pre-proofed dough samples were transferred to a polyethylene bag and then stored in a −20° C. freezer for a period of up to 4 weeks. One day and 4 weeks after preparation, dough samples were thawed at 32° C., about 75% relative humidity for 30-35 min and tested for $CO_2$ release during 60 min incubation at 37° C., using the ANKOM$^{RF}$ Gas Production Measurement System. The measurements were carried out, and the total gas volume produced after 1 day and after 4 weeks storage at −20° C. was measured. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least 2 h one freezing/thawing cycle. Table 15B shows the results obtained.

TABLE 15B

Persistence of fermentative ability after 1 day and 4 weeks of
1% sugar Pre-proofed dough freezing using 7% yeast (30% solids)

|  | 1 day storage [ml $CO_2$/hr/70 gr dough] | 4 weeks storage with freezing/ thawing cycles | 4 weeks storage with freezing/ thawing cycles % from 1 day storage |
|---|---|---|---|
| KF-06 | 227 | 216 | 95 |
| Commercial baker's yeast used in frozen dough | 227 | 148 | 65 |

The experiment shows that the novel yeast strains of the invention may advantageously tolerate long term frozen storage of 1% sugar pre-proofed frozen dough, optionally with multiple freezing/thawing cycles better than commercially available yeast strains, e.g., showing at least 80%, preferably, at least 90%, at least 95% fermentative ability after 4 weeks storage at −20° C. with freezing/thawing cycles of the fermentative ability after 1 day of storage at −20° C.

4.4 Pre-Proofed Mini Loafs 6% Sugar, Frozen Dough

Yeast cultures obtained in Example 3 and commercial yeast product were used for preparation of high sugar dough containing about 6% (w/w of flour) sugar, 1.5% (w/w of flour) salt, 3.5% (w/w of flour) yeast (30% solids), 5% (w/w of flour) fat, 52% (w/w of flour) of water using a bright white wheat flour.

Dough was prepared, divided to portions of 75 g, molded and proofed in a proofing chamber for 25 min at 35° C. and 25 min at room in 20° C., and then frozen to −20° C. using a blast freezer, transferred to polyethylene bags and then stored in a −20° C. freezer for a period of up to 8 weeks. One day, 2 weeks, 4 weeks, and 8 weeks after preparation, dough samples were thawed at 25° C. for 20-30 min and tested for $CO_2$ release during 90 min incubation at 37° C., using the ANKOM$^{RF}$ Gas Production Measurement System. The measurements were carried out, and the total gas volume of fresh dough, after 1 day, after 2, 4, and 8 weeks storage at −20° C. was measured. Table 16 shows the results obtained.

TABLE 16

Persistence of fermentative ability after 2, 4, and 8
weeks of freezing of 6% sugar Pre-proofed mini-loafs.

| Yeast strain | 2 weeks | 4 weeks | 8 weeks |
|---|---|---|---|
| CC-05 | 100% | 81% | 71% |
| Commercial baker's yeast used in frozen dough | 84% | 58% | 44% |

4.5 15% Sugar, Frozen Dough:

4.5.1 Yeast cultures obtained in Example 3 were used for preparation of high sugar dough containing about 15% (w/w of flour) sugar, 1.5% (w/w of flour) salt, 6% (w/w of flour) yeast (30% solids), 50% (w/w of flour) of water using a bright white wheat flour.

Dough was prepared, divided to portions of 50 g and molded, few fresh dough units were tested for $CO_2$ release, and the other units were frozen to −20° C. using a blast freezer, transferred to a polyethylene bag and then stored in a −20° C. freezer for a period of up to 12 weeks. One day, 2, 8 and 12 weeks after preparation, dough samples were thawed at 25° C. for 20-30 min and tested for $CO_2$ release during 60 min incubation at 37° C., using the ANKOM$^{RF}$ Gas Production Measurement System. The measurements were carried out, and the total gas volume of fresh dough, after 1 day, after 2, 8 and 12 weeks storage at −20° C. was measured. To test the ability to withstand multiple freezing/thawing cycles, in a parallel experiment 10 cycles of thawing/freezing were performed during the first 2 weeks of storage, wherein doughs were transferred to 25° C. for 30 min and returned to −20° C. for at least 2 h for one freezing/thawing cycle. Table 17A shows the results obtained.

TABLE 17A

Persistence of fermentative ability after 2, 8 and 12 weeks
of 15% sugar dough freezing using 6% yeast (30% solids).

|  | Fresh dough ml $CO_2$/ hr/100 gr | 2 weeks storage | 2 weeks storage with freezing/ thawing cycles | 8 weeks storage | 12 weeks storage |
|---|---|---|---|---|---|
|  |  |  | % from 1 day measurement |  |  |
| OL-01 | 270 | 100% | 76% | 73% | 65% |
| IS-310 | 206 | 95% | 89% | 81% | 68% |
| FTY-3 (BP FERM 2363) strain | 126 | 55% | 65% | 47% | 32% |

4.5.2 In alternative settings, yeast cultures obtained in Example 3 and commercial yeast product were used for preparation of high sugar dough containing about 15% (w/w of flour) sugar, 2.5% (w/w of flour) salt, 7% (w/w of flour) yeast (30% solids), 6% (w/w of flour) eggs, 14% (w/w of flour) fat, 25% (w/w of flour) of water and 25% (w/w of flour) of milk using a bright white wheat flour.

Dough was prepared, placed to rest for 20 min at room temperature, divided to portions of 50 g, molded and incubated in −20° C. freezer for 2 hours, transferred to a polyethylene bag and then stored in a −20° C. freezer for a period of up to 20 weeks. One day, 2, 11 and 20 weeks after preparation, dough samples were thawed at 25° C. for 20-30 min and tested for $CO_2$ release during 90 min incubation at 37° C., using the ANKOM$^{RF}$ Gas Production Measurement System. The measurements were carried out, and the total gas volume of 1 day, 2, 11 and 20 weeks storage at −20° C. was measured. Table 17B shows the results obtained.

TABLE 17B

Persistence of fermentative ability after 2, 11 and 20 weeks
of 15% sugar dough freezing using 7% yeast (30% solids)

|  | Day 1 ml $CO_2$ | 2 weeks storage | 11 weeks storage | 20 weeks storage |
|---|---|---|---|---|
|  |  | % from 1 day measurement |  |  |
| KF-06 | 204 | 97% | 82% | 63% |
| Commercial baker's yeast used in frozen dough | 226 | 88% | 54% | 39% |

The experiment shows that the novel yeast strains of the invention may advantageously tolerate long term frozen storage of high sugar content (e.g., 15% sugar) frozen dough, optionally with multiple freezing/thawing cycles better than commercially available yeast strains, e.g., showing at least 80%, preferably, at least 90%, or at least 95% fermentative ability after 2 weeks storage at −20° C. of the fermentative ability after 1 day of storage at −20° C., at least 70%, preferably at least 75% or at least 80% fermentative ability after 2 weeks storage at −20° C. with freezing/ thawing cycles of the fermentative ability after 1 day of storage at −20° C., at least 65%, preferably, at least 70% or at least 75% fermentative ability after 8 weeks storage at −20° C. with freezing/thawing cycles of the fermentative ability after 1 day of storage at −20° C. or at least 60%, preferably at least 63% or at least 65% fermentative ability after 12 weeks storage at −20° C. with freezing/thawing cycles of the fermentative ability after 1 day of storage at −20° C. Also, novel yeast strains preferably demonstrate at least 68%, preferably 72%, preferably 78% or at least 82% fermentative ability after 11 weeks storage of frozen 15% sugar dough at −20° C. of the fermentative ability after 1 day of storage at −20° C. The said strains also preferably demonstrate at least 50%, preferably at least 55%, at least 60% or at least 63% fermentative ability after 20 weeks storage of frozen 15% sugar dough at −20° C. of the fermentative ability after 1 day of storage at −20° C.

Example 5

Scoring of Fermentative Performance 5.1 Yeast cultures were propagated on 5 mL YPD substrate for 15 h in a shaker-incubator at 30° C. and at 200 rpm, harvested and suspended in fresh YPD medium to the concentration of 5 $OD_{600}$. The 5 mL yeast suspensions in a 50 ml centrifuge tube (PP, Miniplast, Ein Shemer) were frozen at −18° C. for 3 days, thawed for 20 min at room temperature and tested for their fermentative ability in a liquid flour suspension (LFS). The yeast samples were washed twice with distilled water, using a centrifugation at 4° C. and 1300 g for 8 min. The cultures were suspended in 10 mL lean (i.e. non-sugar) LFS (7.2 g water, 0.23 g salt, 2.57 g white bright wheat flour) and incubated in a shaker-incubator at 37° C. and at 100 rpm. The LFS samples were (optionally) evaluated every 30 min. while a final grade was given after 90 min. The yeast fermentative performance was graded from 0 to 5 according to the following score: the grade was scored according to 4 parameters: time (1 point), bubbles loosed into a aqueous phase (1 point), holes inside the flour's sediment (1.5 points) and foam on the top of aqueous phase (1.5 point).

Time: Yeast strains that initiated fermentation after 30 min of incubation received 1 point, while yeast strains that started to ferment after 60 min received 0.5 point and yeast strains with delayed initiation after 90 min did not receive any point. Fermentation initiation was determinate by visual inspection of flour sediment and the presence of holes.

Bubbles: Samples without appearance of bubbles in the liquid phase did not receive any points, samples with a small number of bubbles (i.e., one bubble released into the liquid phase every 5-10 sec) received 0.5 point, while LFS with a lot of bubbles (at least one bubble released into the liquid phase every 2-5 sec) received 1 point.

Holes: LFS samples without holes in the solid phase did not receive points. LFS with small holes (below 1.5 mm in diameter) received 0.5 point, and LFS with large holes (1.5-2.5 mm in diameter) received 1 point. LFS with large connected holes (diameter greater than 5 mm) received 1.5 points.

Foam: LFS samples without foam on top of the liquid phase didn't receive any points. LFS with thin foam layer below 3 mm received 0.5 point, LFS with a thick layer of foam (3-5 mm) received 1 point and LFS with foam layer thicker than 5 mm received 1.5 points.

The results are shown in Table 18.

TABLE 18

Fermentative performance score of new improved yeasts

| Yeast strain | Score | |
|---|---|---|
| | Before freezing | After 3 days of freezing |
| OL-01 | 3.5 | 1.5 |
| S3-02 | 4 | 3 |
| IS-310 | 2.5 | 2.5 |
| CC-05 | 4.5 | 3.5 |
| KF-06 | 4 | 2 |
| Commercial baker's yeast strain used in frozen dough- | 3.5 | 0 |

5.2 In alternative settings, yeast cells were propagated on 50 mL YPD substrate for 18-24 h in a shaker-incubator at 30° C. and at 200 rpm, harvested and washed twice with cold distilled water using a centrifugation at 4° C. and 1300 g for 8 min. Density of washed cultures was measured and cells portion of about 32 $OD_{600}$ was suspended in 10 ml of LFS (as described in 5.1). For each yeast culture, one LFS sample was tested immediately and another sample was incubated in −20° C. for 2-3 days, thawed for 45 minutes in room temperature, vortex and yeast ability to ferment LFS was tested to assess fermentative performance LFS samples were incubated in a shaker-incubator at 37° C. and at 100 rpm for 1 hour. The yeast fermentative performance was graded from 0 to 9 according to the following score, based on four parameters: bubbles released into the aqueous phase (1.5 point), holes inside the flour's sediment and spongy dough appearance (4 points), foam on the top of the aqueous phase (1.5 point) and phase separation (2 points).

Bubbles: Samples without appearance of bubbles in the liquid phase did not receive any points, samples with a small number of bubbles (no bubbles released into liquid phase, however, small amount of bubbles were detected on the top of the aqueous phase) received 0.5 point, samples with a medium number of bubbles (i.e., one bubbles released every 5 sec) received 1 point, while LFS with a lot of bubbles (at least two bubbles released into the liquid phase every 5 sec) received 1.5 point.

Holes: LFS samples without holes in the solid phase did not receive points. LFS with low number of small holes (below 1.5 mm in diameter) received 0.5 point, high amount of small holes—1 point, LFS with small amount of large holes (1.5-2.5 mm in diameter) received 1.5 points and high amount of large holes—2 points. LFS with sponge dough appearance (connected holes with diameter greater than 5 mm) not more than 25% of LFS received 2.5 points. LFS with sponge dough appearance in restricted area received 3 points. LFS with medium sponging (approximately half of the media displayed spongy appearance)—received 3.5 points. LFS sample completely spongy—received 4 points.

Foam: LFS samples without foam on the top of liquid phase didn't receive any points. LFS with thin foam layer ~1 mm received 0.5 point, LFS with a medium layer of foam (1-3 mm) received 1 point and LFS with thick foam layer thicker than 3 mm received 1.5 points.

Phase separation: Phase separation is a situation in which bubbles and pieces of liquid dough form third layer in addition to a solid and a liquid phase. Samples which displayed phase separation with third layer thickness less than 0.5 cm received 1 points, samples which displayed phase separation with third layer thickness between 0.5 and 1 cm received 1.5 points, samples which displayed phase separation with third layer thickness more than 1 cm received 2 points.

The results are shown in Table 19.

TABLE 19

Fermentative performance score of new improved yeasts

| Yeast strain | scoring | | Persistence of fermentative ability after 2 day freezing |
|---|---|---|---|
| | Before freezing | After freezing | (% from before freezing scoring) |
| Commercial baker's yeast strain from producer A | 9 | 3 | 33% |
| OL-01 | 5.5 | 3 | 55% |
| CC-05 | 9 | 9 | 100% |

Example 6

Yeast Survival Test

*Saccharomyces cerevisiae* strains OL-01, S3-02, FL-03, IS-310, CC-05, KF-06, commercial baker's yeast strain used in frozen dough and freeze resistant strain FTY-3 (FERM BP 2363 (U.S. Pat. No. 5,352,606 B1)) were grown on YPD medium, harvested and re-suspended in fresh YPD medium to a concentration of 5 $OD_{600}$. A sample was taken from each yeast suspension and immediately seeded on YPD agar plates to determinate the initial number of colonies. 5 mL yeast suspensions in a 50 ml centrifuge tube (PP, e.g., from Miniplast, Ein Shemer) were incubated in −20° C. for 48-72 hours, followed by four freezing/thawing cycles (1.5 h in 30° C./at least 1 h in −20° C.). Viable yeast counts were measured using seeding decimal dilutions of yeast suspensions on YPD agar plates and incubation in 30° C. for 48 hours.

Survival rate was determined as follows:

Survival rate=Final number of yeast colonies/Initial number of yeast colonies×100%

Figure 1B:
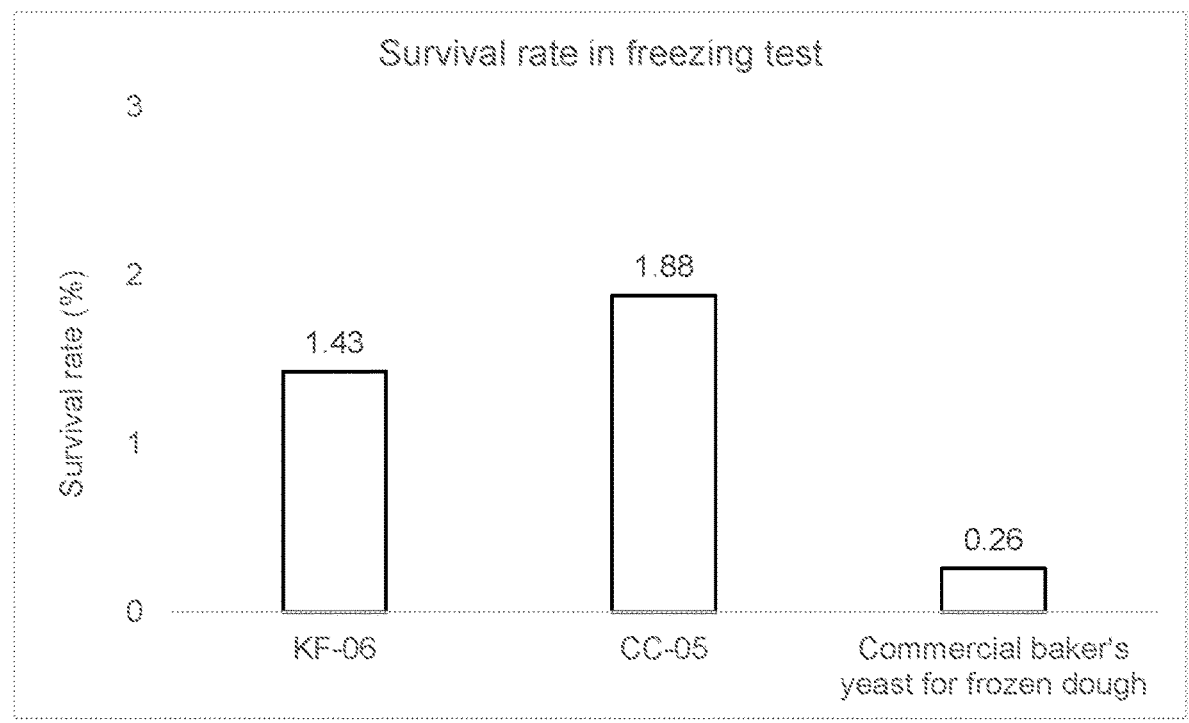

The results are shown in FIGS. 1A and B.

Example 7

Baking Test of Frozen Dough 7.1. Mini Loaf Volume:

Non-sugar dough samples (50 g) obtained as in Example 4.1.1 after 1 day storage at −20° C. and after 4 weeks storage at −20° C. with freezing and thawing cycles (as described in Example 4.1) were thawed at 25° C. for 20-30 min and proofed in a proofing chamber with above 85% relative humidity at 35° C. for 70 min, and then baked in mini loaf pans at 195° C. for 7-8 min. Mini loafs apparent volume was measured after cooling to room temperature according to a solids displacement method used to measure the volume of irregular solids (Physical Properties of Foods, Serpil Sahin, Servet Gulum Sumnu, page 20) using poppy seeds. The results are shown in FIG. 2.

7.2. Pre-Proofed Mini Loaf Volume:

Non-sugar dough samples (50-80 g) obtained as in Example 4.2 after 1 day storage at −20° C. and after 4 weeks storage at −20° C. frozen pre-proofed mini loafs were directly baked, no thawing stage, according to the following baking program:

| Temp. | Steam | Time |
|---|---|---|
| 90° C. | + | 4 min |
| 110° C. | + | 6 min |
| 190° C. | − | 11 min |
| 185° C. | − | 4 min |

Mini loafs apparent. volume was measured after cooling to room temperature according to a solids displacement method used to measure the volume of irregular solids (Physical Properties of Foods, Serpil Sahin, Servet Gulum Sumnu, page 20) using poppy seeds. The results are shown in FIG. 3.

7.3. Mini Loaf Proofing Time:

Non-sugar dough samples (50 g) obtained as in Example 4.1 after 4 weeks storage at −20° C., optionally, with freezing and thawing cycles (as described in Example 4.1), were thawed at 25° C. for 20-30 min and proofed in a proofing chamber at 35° C. until they reached a predetermined height of 3.5 cm in a clear plastic box having the dimensions 5.8×8.6×4.5 W×L×H [$cm^3$] maximally, for 120 min. The results are shown in Table 20.

TABLE 20A

Proofing time after 4 weeks freezing and 4 weeks freezing with freezing and thawing cycles

| | 4 weeks storage | 4 weeks with freezing and thawing cycles |
|---|---|---|
| OL-01 | 65 min | 102 min |
| KF-06 | 85 min | 103 min |
| CC-05 | 85 min | 98 min |
| Commercial baker's yeast used in frozen dough | 95 min | 120 min |
| Commercial baker's yeast from producer A | 90 min | >120 min |

In alternative setting, non-sugar dough samples (50 g) obtained as in Example 4.1 after 24 weeks storage at −20° C. were thawed at 25° C. for 20-30 min and proofed in a proofing chamber at 35° C. until they reached a predetermined height of 3.5 cm in a clear plastic box having the dimensions 5.8×8.6×4.5 W×L×H [$cm^3$] maximally, for 120 min. The results are shown in Table 20B.

TABLE 20B

Proofing time after 24 weeks freezing

| | 24 weeks storage |
|---|---|
| KF-06 | 90 min |
| CC-05 | 105 min |
| Commercial baker's yeast used in frozen dough | >120 min |

The baking data above strengthens the data presented in previous examples that the novel yeast strains of the invention may advantageously tolerate long term frozen storage, optionally with multiple freezing/thawing cycles better than commercially available yeast strains, e.g., showing the smallest rate of mini loaf volume decrease after 4 weeks storage at −20° C. with freezing/thawing cycles and the shortest proofing time after 4 weeks storage at −20° C. and after 4 weeks storage at −20° C. with freezing/thawing cycles in comparison to the commercial yeast strains presented above.

Example 8

Genomic markers of the generated yeast strains were analyzed. Genomic DNA was prepared for sequencing using the Nextera XT kit (Illumina, San Diego, Calif.) according to the manufacturer's instructions. After processing, libraries were assessed for size using an Agilent TapeStation 2000 automated electrophoresis device (Agilent Technologies, Santa Clara, Calif., and for concentration by a Qubit fluorometer (Thermo Fisher Scientific Inc., Waltham, Mass. and for concentration. DNA libraries were pooled in equimolar ratio and sequenced using an Illumina NextSeq500 sequencer, with paired-end 2×150 base reads. Raw reads from novel genomes were mapped to the S288C yeast reference genome (https://www.ncbi.nlm.nih.gov/genome/15?genome_assembly_id=22535). Bioinformatics analysis was done providing at least 1000 bp long contigs using coverage of at least 250×. Copy number variations were assessed individually for each genome based on coverage, looking for large-scale fluctuations from the genome-wide median. Deleted regions of the novel strains genome were assessed.

Novel Strains CC-05, KF-06 and OL-01 were found to be characterized by mutations, often, deletions, of genomic DNA fragments from the same genes in all alleles, as described below and/or by inactivation of the same genes in all alleles. In contrast, in the yeast strain S288C used in the systematic sequencing project for the Saccharomyces Genome Database, there are no deletions or inactivating mutations in said genes. All mutations or modifications referred to herein relate to comparison with S288C.

- Gene YDL248W named COS7 located at Chromosome IV is partially deleted downstream to position 2232 (deletion length is at least 150 bp);
- Gene YJR155W named AAD10 located at Chromosome X is partially deleted downstream to position 727404 (total deletion length is at least 360 bp);
- Gene YDL245C named HXT15 located at Chromosome IV is partially deleted downstream to position 11657 in all alleles (total deletion length is at least 400 bp);
- Gene YJR151C named DAN4 located at Chromosome X comprises mutations leading to two stop codons, at amino acid position 342 (exchange of Serine to stop codon) and at amino acid position 53 (exchange of Tyrosine to stop codon), and at least partial deletion(s) and/or genomic rearrangement, e.g., between coordinates of Chromosome X:714,902-715,267 (these are the coordinates in reference strain S288C);
- Gene YDR420W located at Chromosome IV contains a number of single mutations leading to amino acids exchanges, such as mutations at position 1308583 and at position 1308589, which result in exchange from Serine to Proline and mutations at position 1308951 and at position 1309390 which result in exchange from Phenylalanine to Leucine.

Example 9

Preferred yeast strains of the invention, e.g., the CC-05 and KF-06 strains, can be characterized as comprising all of the below three DNA segments, as detailed in Table 21, with optional variations between alleles in at most three, preferably, at most one base pair(s). The sequences were obtained by using polymerase chain reaction (PCR) followed by Sanger sequencing. Sanger sequencing was performed using Big-Dye terminator sequencing on a 3730xl capillary electrophoresis device (Applied Biosystems, ThermoFisher Scientific). The PCR was done based on the amplification of specific primers designed for amplification of the said genomic DNA fragments as disclosed below. Table 21 presents the chromosome and position, unique sets of primers used and the three amplified genomic DNA fragments present in CC-05 and KF-06. All alleles of said strains contain the sequences of table 21, with optional changes in one basepair, wherein the change preferably only is in one allele of one of the genes.

TABLE 21

| PCR Results from PCR Amplicons for Genomes of CC-05 and KF-06 strains |||
|---|---|---|
| Chromosome and position | Primers | Sequence |
| VII: 682038-682789 | Primer 1: CTGTATGGTTC GCCGTTTAT (SEQ ID NO: 1) Primer 2: GGTAATCTGT GGGATGTAAC TG (SEQ ID NO: 2) | CTGTATGGTTCGCCGTTTATTTTCTAAGCACCG TTTTTTATTCATATTTTTATAATGCAACTCCTA TAGAATATAGATGTTTCGTGTTTTTAATTCCTG CTATGACTTTGTGTCAATGGTATGTGAACTAA CAACTGTGTGGTAGTTTGGGATGGTACGTAAA GGTGTTCGTGATTATATAAGCAATCTTAAAAT ATTTGTATCGCACCATGAGGTGCCCAATAATG AAATGAAAATTACTATTATGAACTATACTAAA AAGATGAAACTTTTTTATCAATCCCAGGTTCTT TTACTTATTATTTTTGGATATAAGAACAAAATC GGATTTCCCATGCTTTTTCTCAATGTCTATATG AAATCTTTTCGAAACAGCCAGTACATGTAACA ATTATGATACGAACTTGATCGGTAACCCATAA ATAACAGGAGCTGCGCCGTTCAAGTAACGTAG ATGGCATACACCTCTAGATTTAGAGACGGCAT ATGAAACAGATAGGCTATTACCATTCAAATCG TCAGTATTACAGCGAAATCCCATCTTTTCAAA AAGTTCCTCGCTAAATTTATCAATATCTTTGTC AGTTACATCCCACAGATTACC (SEQ ID NO: 7) |
| IV: 220222-220627 | Primer 1: ATTGCCTCTCA GTATCGT (SEQ ID NO: 3) | ATTGCCTCTCAGTATCGTAATTCTATGTGGGTA TCTGACTTTCATGGCAACTAGGTAAGATACAG TTTCAACAGAATAATATCCTCTATCCACGTAA TCACCCATGAAAAGGTAATTGGTGTCAGGACA |

TABLE 21-continued

PCR Results from PCR Amplicons for Genomes of CC-05 and KF-06 strains

| Chromosome and position | Primers | Sequence |
|---|---|---|
| | Primer 2: CACAAATCTT CCAAACCAC (SEQ ID NO: 4) | AGGACCACCAATCTTGAAAAGTTCTAACAAGT CATGGAATTGACCGTGTACGTCACCACAAATA GTAACAGGCACATTAATTGGTTTAACATTTTC CTCGAACTGCAACACGTCCACCGCCATTTTAC ATAGTCGTGCTACATCGTCTTCTGATAGTGGCT CGCATTTACTCAAATGCTCAATCCATTGGTCA AGCTGATTTATATTTGTGTTATTCAGTTCTAGT GGTTTGGAAGATTTGTG (SEQ ID NO: 8) |
| XI: 290975-291685 | Primer 1: CGCTGTAGCA AAGCAAAAAG (SEQ ID NO: 5) Primer 2: GCAATGACCG TAGGAGTGA (SEQ ID NO: 6) | CGCTGTAGCAAAGCAAAAGTTTCTGATTCAA AATAAGTCACCTACTCTTAGCGCATTTTTATTG TATATAAAGGCATTTAATGTAATTTATAGAGC ATTATAAATCGTAACAACTACTGCAGTATGAG TTTCATGAATTCATTTCTCGATATCTTATGAAT ATACACAGGTATATATGTATATTCATGTTAAA CGCCTTTCGAATTGTTCGTTGGCTTTTTTTGTG AAATTATCTCGGGAAAAGGGCGAAATTATATC GTTTTGCCGTTGATATTTTGAAAAGGAATAAA AGATCATGAAAAAAATAAGAAAGGCAATTCG ACGCATTTCTCTCAGCAAGCTATTCTTTACTTT TGAAGAATAAAATATTTGAGTAAAAAGGTTAA GACAATATAGTCGGAAGCAGTTCTGCGGGATC TGAAGGAATTGCGGAATAATGAGATTTCACGA TAGTATACTTATCTTCTTTTCTTTGGCATCGCT TTATCAACATGTTCATGGTGCAAGACAAGTCG TTCGTCCAAAGGAGAAAATGACTACTTCAGAA GAAGTTAAACCTTGGTTACGTACGGTTTATGG AAGTCAAAAGAATTAGTCACTCCTACGGTCA TTGC (SEQ ID NO: 9) |

PCR was carried out after preparation of DNA from yeast using standard protocols (DreamTaq Green PCR Master Mix (2×), ThermoFisher Scientific, Waltham, Mass.), with 1.4 ng DNA under the following conditions: initial denaturation at 95° C. for 5 minutes, followed by 30 cycles of 95° C. denaturation for 30 seconds, 55° C. or 60° C. annealing for 45 seconds, and 72° C. elongation for 1 minute.

The invention claimed is:

1. A baker's yeast strain obtained by breeding between a first strain selected from the group consisting of OL-01 deposited as NCYC 4095, S3-02 deposited as NCYC 4094, FL-03 deposited as NCYC 4105, IS-310 deposited as NCYC 4106, CC-05 deposited as NCYC 4128 and KF-06 deposited as NCYC 4129 and a second Saccharomyces cerevisiae strain selected from the group consisting of OL-01 deposited as NCYC 4095, S3-02 deposited as NCYC 4094, FL-03 deposited as NCYC 4105, IS-310 deposited as NCYC 4106, CC-05 deposited as NCYC 4128 and KF-06 deposited as NCYC 4129.

2. The baker's yeast strain of claim 1, wherein the baker's yeast strain is capable of surviving with a survival rate of at least 1%, has a regimen comprising:
   a) growing the yeast strain on YPD medium for 15 h in a shaker-incubator at 30° C. and 200 rpm,
   b) harvesting the yeast and re-suspending in fresh YPD medium to a concentration of 5 $OD_{600}$,
   c) incubating 5 mL yeast suspensions in 50 mL tubes at −20° C. for 48-72 h,
   d) followed by four freezing/thawing cycles, each freezing/thawing cycle comprising 1.5 h at 30° C. and 200 rpm, and 1 h at −20° C.,
   wherein the survival rate is determined as the number of viable yeast colonies after said freeze/thawing cycles/number of viable yeast colonies before said freeze/thawing cycles×100%, and wherein the number of viable yeast colonies is measured using seeding decimal dilutions of yeast suspensions on YPD agar plates and incubation at 30° C. for 48 hours.

3. The baker's yeast strain of claim 1,
   wherein the baker's yeast strain shows at least 90% fermentative ability after storage of a dough prepared with said yeast strain at −20° C. for 4 weeks compared to its fermentative ability after storage of said dough at −20° C. for 1 day,
   wherein, optionally, the baker's yeast strain shows at least 73% fermentative ability after storage of a dough prepared with said yeast strain at −20° C. for 4 weeks with 10 freezing/thawing cycles performed during the first 2 weeks of storage,
   wherein the dough is transferred to 25° C. for 30 min and returned to −20° C. for at least 2 h for one freezing/thawing cycle, compared to its fermentative ability after storage of said dough at −20° C. for 1 day.

4. A yeast product comprising yeast of a baker's yeast strain of claim 1, wherein the yeast product is selected from the group consisting of cream yeast, compressed yeast, crumbled yeast, semi active dry yeast, instant dry yeast, active dry yeast and frozen yeast.

5. A dough or dough product comprising the yeast product of claim 4.

6. A baker's yeast strain, wherein the baker's yeast strain is OL-01 deposited as NCYC 4095, S3-02 deposited as NCYC 4094, FL-03 deposited as NCYC 4105, IS-310 deposited as NCYC 4106, CC-05 deposited as NCYC 4128 or KF-06 deposited as NCYC 4129.

7. The baker's yeast strain of claim 6, wherein the baker's yeast strain is CC-05 deposited as NCYC 4128.

8. The baker's yeast strain of claim 6, wherein the baker's yeast strain is capable of surviving with a survival rate of at least 1%, has a regimen comprising:
   a) growing the yeast strain on YPD medium for 15 h in a shaker-incubator at 30° C. and 200 rpm,
   b) harvesting the yeast and re-suspending in fresh YPD medium to a concentration of 5 $OD_{600}$,
   c) incubating 5 mL yeast suspensions in 50 mL tubes at −20° C. for 48-72 h,
   d) followed by four freezing/thawing cycles, each freezing/thawing cycle comprising 1.5 h at 30° C. and 200 rpm, and 1 h at −20° C.,
   wherein the survival rate is determined as the number of viable yeast colonies after said freeze/thawing cycles/ number of viable yeast colonies before said freeze/ thawing cycles×100%, and wherein the number of viable yeast colonies is measured using seeding decimal dilutions of yeast suspensions on YPD agar plates and incubation at 30° C. for 48 hours.

9. The baker's yeast strain of claim 6,
   wherein the baker's yeast strain shows at least 90% fermentative ability after storage of a dough prepared with said yeast strain at −20° C. for 4 weeks compared to its fermentative ability after storage of said dough at −20° C. for 1 day,
   wherein, optionally, the baker's yeast strain shows at least 73% fermentative ability after storage of a dough prepared with said yeast strain at −20° C. for 4 weeks with 10 freezing/thawing cycles performed during the first 2 weeks of storage,
   wherein the dough is transferred to 25° C. for 30 min and returned to −20° C. for at least 2 h for one freezing/ thawing cycle, compared to its fermentative ability after storage of said dough at −20° C. for 1 day.

10. A yeast product comprising yeast of a baker's yeast strain of claim 6, wherein the yeast product is selected from the group consisting of cream yeast, compressed yeast, crumbled yeast, semi active dry yeast, instant dry yeast, active dry yeast and frozen yeast.

11. A dough or dough product comprising the yeast product of claim 10.

* * * * *